US010949790B2

(12) United States Patent
Gutman et al.

(10) Patent No.: US 10,949,790 B2
(45) Date of Patent: Mar. 16, 2021

(54) SYSTEMS AND METHODS FOR IMPROVING COMMUNICATION EFFICIENCY AND REDUCING DATA REDUNDANCY IN A COMPUTERIZED PLATFORM

(71) Applicant: HealthTap, Inc., Mountain View, CA (US)

(72) Inventors: Ron J. Gutman, Atherton, CA (US); Geoffrey W. Rutledge, Menlo Park, CA (US); Sean K. Mehra, San Francisco, CA (US)

(73) Assignee: HEALTHTAP, INC., Mountain View, CA (US)

( * ) Notice: Subject to any disclaimer, the term of this patent is extended or adjusted under 35 U.S.C. 154(b) by 0 days.

(21) Appl. No.: 16/849,468

(22) Filed: Apr. 15, 2020

(65) Prior Publication Data
US 2020/0294683 A1 Sep. 17, 2020

Related U.S. Application Data

(60) Continuation of application No. 15/851,189, filed on Dec. 21, 2017, now abandoned, which is a division of
(Continued)

(51) Int. Cl.
*G06Q 10/06* (2012.01)
*G16H 70/00* (2018.01)
(Continued)

(52) U.S. Cl.
CPC ..... *G06Q 10/06393* (2013.01); *G06F 3/0482* (2013.01); *G06F 16/9024* (2019.01);
(Continued)

(58) Field of Classification Search
CPC ........ G16H 80/00; G16H 40/20; G16H 70/00; G16H 40/67; G16H 70/20; H04L 67/12;
(Continued)

(56) References Cited

U.S. PATENT DOCUMENTS

| 5,908,383 A | 6/1999 | Brynjestad |
| 6,687,685 B1 | 2/2004 | Sadeghi et al. |

(Continued)

FOREIGN PATENT DOCUMENTS

| EP | 1853050 A1 * | 11/2007 | .......... H04M 3/4285 |
| WO | 2007/145650 A2 | 12/2007 | |
| WO | 2010045191 A2 | 4/2010 | |

OTHER PUBLICATIONS

Nehme, Efficient Query Processing for Rich and Diverse Real-Time Data, Aug. 2009, UMI Dissertation Publishing ProQuest, pp. 1-226. (Year: 2009).*

(Continued)

*Primary Examiner* — Christopher L Gilligan
(74) *Attorney, Agent, or Firm* — Seed IP Law Group LLP

(57) ABSTRACT

An example method for improving communication efficiency and reducing data redundancy in a computerized platform includes determining a priority value of an inquiry based on a duration of time for which the inquiry remains unanswered in the queue in comparison with other unanswered inquiries, sorting previously-obtained inquiries based on (a) a quantity of common topic labels shared between the set of topic labels associated with the inquiry and a respective set of topic labels associated with each previously-obtained inquiry in the subset and (b) a quality score associated with an answer to each previously-obtained inquiry in the subset to generate a sorted list for presentation, and routing the inquiry based on (a) user interactions, (b) the priority value of the inquiry, and (c) at least one of a user request, relation to a specialty of a healthcare professional,
(Continued)

geographic location of the healthcare professional, or history of answers provided by the healthcare professional.

15 Claims, 10 Drawing Sheets

Related U.S. Application Data application No. 14/320,241, filed on Jun. 30, 2014, now abandoned.

(60) Provisional application No. 61/841,145, filed on Jun. 28, 2013, provisional application No. 61/841,174, filed on Jun. 28, 2013, provisional application No. 61/841,151, filed on Jun. 28, 2013.

(51) Int. Cl.
| | |
|---|---|
| *G16H 40/20* | (2018.01) |
| *G16H 80/00* | (2018.01) |
| *G06F 16/901* | (2019.01) |
| *G06F 3/0482* | (2013.01) |
| *H04L 29/08* | (2006.01) |
| *G16H 40/67* | (2018.01) |
| *G16H 70/20* | (2018.01) |

(52) U.S. Cl.
CPC .............. *G16H 40/20* (2018.01); *G16H 40/67* (2018.01); *G16H 70/00* (2018.01); *G16H 70/20* (2018.01); *G16H 80/00* (2018.01); *H04L 67/12* (2013.01)

(58) Field of Classification Search
CPC .............. G06F 3/0482; G06F 16/9024; G06Q 10/06393
See application file for complete search history.

(56) References Cited

U.S. PATENT DOCUMENTS

| | | | |
|---|---|---|---|
| 8,010,460 B2 | 8/2011 | Work et al. | |
| 8,341,167 B1 | 12/2012 | Podgorny et al. | |
| 8,346,573 B2 | 1/2013 | Glimp et al. | |
| 8,484,186 B1 | 7/2013 | Kapczynski et al. | |
| 8,548,870 B1 | 10/2013 | Herbette et al. | |
| 8,732,096 B1 | 5/2014 | Glukhov | |
| 2001/0037219 A1 | 11/2001 | Malik | |
| 2002/0052773 A1 | 5/2002 | Kraemer et al. | |
| 2003/0028399 A1 | 2/2003 | Davis et al. | |
| 2003/0088458 A1 | 5/2003 | Afeyan et al. | |
| 2005/0015115 A1 | 1/2005 | Sullivan et al. | |
| 2005/0060187 A1 | 3/2005 | Gottesman | |
| 2005/0251423 A1 | 11/2005 | Bellam et al. | |
| 2006/0036430 A1 | 2/2006 | Hu | |
| 2006/0036619 A1 | 2/2006 | Fuerst et al. | |
| 2006/0100901 A1 | 5/2006 | Glimp et al. | |
| 2006/0161456 A1 | 7/2006 | Baker et al. | |
| 2006/0271400 A1 | 11/2006 | Clements et al. | |
| 2006/0277075 A1 | 12/2006 | Salwan | |
| 2007/0022109 A1 | 1/2007 | Imielinski et al. | |
| 2007/0033005 A1 | 2/2007 | Cristo et al. | |
| 2007/0185732 A1 | 8/2007 | Hicks et al. | |
| 2007/0219854 A1 | 9/2007 | Mueller et al. | |
| 2007/0232686 A1 | 10/2007 | Reiner | |
| 2008/0133290 A1 | 6/2008 | Siegrist et al. | |
| 2008/0201429 A1 | 8/2008 | Barbell et al. | |
| 2008/0275311 A1 | 11/2008 | Haq | |
| 2009/0012833 A1 | 1/2009 | Kuhlke et al. | |
| 2009/0063188 A1 | 3/2009 | Schoenberg | |
| 2009/0100269 A1 | 4/2009 | Naccache | |
| 2009/0164252 A1 | 6/2009 | Morris et al. | |
| 2010/0174555 A1 | 7/2010 | Abraham-Fuchs et al. | |
| 2010/0217619 A1 | 8/2010 | Cox et al. | |
| 2011/0066954 A1 | 3/2011 | Zuber | |
| 2011/0092825 A1 | 4/2011 | Gopinathan et al. | |
| 2011/0093404 A1 | 4/2011 | Lawless et al. | |
| 2011/0112380 A1 | 5/2011 | Robinson | |
| 2011/0119072 A1 | 5/2011 | Lipner et al. | |
| 2011/0191122 A1 | 8/2011 | Kharraz Tavakol et al. | |
| 2011/0288884 A1 | 11/2011 | Algoo et al. | |
| 2011/0302485 A1 | 12/2011 | D'Angelo et al. | |
| 2012/0035959 A1 | 2/2012 | Berdia | |
| 2012/0101847 A1 | 4/2012 | Johnson et al. | |
| 2012/0173992 A1 | 7/2012 | D'Angelo et al. | |
| 2013/0031090 A1 | 1/2013 | Posse et al. | |
| 2013/0060576 A1 | 3/2013 | Hamm et al. | |
| 2013/0096937 A1 | 4/2013 | Campbell et al. | |
| 2013/0110791 A1 | 5/2013 | Cai et al. | |
| 2013/0185231 A1 | 7/2013 | Baras et al. | |
| 2013/0297324 A1 | 11/2013 | Phillips et al. | |
| 2014/0006055 A1 | 1/2014 | Seraly | |
| 2014/0019444 A1* | 1/2014 | Jones .................. | G06F 16/3326 707/723 |
| 2014/0073880 A1 | 3/2014 | Boucher et al. | |
| 2014/0074507 A1* | 3/2014 | Simon .................. | G06F 19/3418 705/3 |
| 2014/0081659 A1 | 3/2014 | Nawana et al. | |
| 2014/0122109 A1 | 5/2014 | Ghanbari et al. | |
| 2014/0143354 A1 | 5/2014 | Tiernan | |
| 2014/0200911 A1* | 7/2014 | Schoenberg .......... | G16H 40/20 705/2 |
| 2014/0258885 A1 | 9/2014 | Etchegoyen | |
| 2014/0280108 A1 | 9/2014 | Dunn et al. | |
| 2014/0288951 A1 | 9/2014 | Zielinski | |
| 2014/0331059 A1 | 11/2014 | Rane et al. | |
| 2014/0354405 A1 | 12/2014 | Kocher et al. | |
| 2014/0379366 A1 | 12/2014 | Alloway et al. | |
| 2015/0006261 A1* | 1/2015 | Gutman .......... | G06Q 10/06393 705/7.39 |
| 2015/0379227 A1 | 12/2015 | Gerard | |
| 2016/0217198 A1 | 7/2016 | Lee et al. | |
| 2017/0262529 A1 | 9/2017 | Chim | |
| 2018/0212782 A1 | 7/2018 | Csik et al. | |

OTHER PUBLICATIONS

Office Action issued in CA application No. 2,916,901, dated May 29, 2020, 5 pages.
Australian Examination Report No. 2 dated Feb. 20, 2020, for Australian Application No. 2014302062, 5 pages.
Extended European Search Report, dated May 27, 2019, for European Application No. 16858160, 14 pages.
International Search Report and Written Opinion, dated Aug. 26, 2020, for International Application No. PCT/US2020/0312521, 10 pages.
Office Action, dated Sep. 10, 2020, for U.S. Appl. No. 16/780,504, Gutman et al., "Systems and Methods for Evaluating and Selecting a Healthcare Professional Using a Healthcare Operating System," 16 pages.
International Preliminary Report on Patentability received for counterpart International Application No. PCT/US2016/057770; dated Apr. 24, 2018, 7 pages.
International Search Report and Written Opinion issued in corresponding application No. PCT/US2014/044925, dated Jan. 29, 2015, 14 pages.
International Preliminary Report on Patentability issued in application No. PCT/US2014/044925, dated Jan. 7, 2016, 10 pages.
EPO Communication and Supplementary Search Report, issued in related application EP 14818817, dated Nov. 9, 2016, 7 pages.
International Search Report and Written Opinion issued in application No. PCT/US16/57770, dated Jan. 23, 2017, 9 pages.
International Preliminary Report on Patentability issued in application No. PCT/US2016/057770, dated May 3, 2018, 8 pages.
Office Action issued in U.S. Appl. No. 14/320,241, dated Jan. 16, 2018, 13 pages.
Office Action issued in U.S. Appl. No. 14/320,241, dated Jun. 25, 2018, 17 pages.
Office Action issued in application No. 14 818 817.0, dated Oct. 21, 2019, 6 pages.

(56) References Cited

OTHER PUBLICATIONS

Extended European Search Report, issued in related application 16 858 160.1, dated Oct. 21, 2019, 16 pages.
International Search Report issued in application No. PCT/US2019/047999, dated Dec. 17, 2019, 11 pages.
Office Action issued in U.S. Appl. No. 15/839,595, dated Dec. 27, 2019, 12 pages.
Office Action issued in U.S. Appl. No. 14/320,241, dated Jan. 24, 2020, 8 pages.
Examination report issued in AU Application No. 2014302062, dated Feb. 20, 2020, 5 pages.
Office Action issued in Application No. U.S. Appl. No. 15/298,099, dated Mar. 23, 2020, 12 pages.
Office Action issued in U.S. Appl. No. 15/839,595, dated Apr. 7, 2020, 14 pages.
Office Action issued in application No. 16858160.1, dated May 27, 2019, 14 pages.
Office Action issued in NZ Application No. 715845, dated Nov. 26, 2019, 4 pages.
Office Action issued in IL application No. 258769, dated Jan. 2, 2020, 4 pages.
Office Action issued in U.S. Appl. No. 15/851,189, dated Mar. 13, 2020, 23 pages.
Office Action issued in U.S. Appl. No. 15/851,226, dated Mar. 24, 2020, 16 pages.
Office Action issued in U.S. Appl. No. 16/239,495, dated Mar. 24, 2020, 24 pages.
Sadeghi et al. "A Bayesian Model for Triage Decision Support." *International Journal of Medical Informatics* 75:403-411, 2006.

\* cited by examiner

SYSTEMS AND METHODS FOR IMPROVING COMMUNICATION EFFICIENCY AND REDUCING DATA REDUNDANCY IN A COMPUTERIZED PLATFORM

TECHNICAL FIELD

The presently disclosed technology relates to communication and data management, and more specifically, systems and methods for improving communication efficiency and reducing data redundancy based on a computerized platform.

BACKGROUND

Currently, the process of choosing a healthcare professional is time consuming, inefficient, and filled with uncertainty. When individuals find themselves in need of medical care, they often have difficult time finding a doctor with whom they will be satisfied. Many individuals select their doctors based on: a referral from a primary care physician, a recommendation from a friend or relative, or a healthcare provider directory. These sources do not provide an objective metric for the quality of the doctor's knowledge as assessed by a broader medical community or based on publicly available information.

Further, patients might look for a healthcare provider directory or some Internet rating website. However, most Internet rating websites provide collections of comments or ratings from unidentified sources and the veracity of data remains unknown to the community. These sources do not provide an objective metric for the quality of the doctor's knowledge as assessed by a broader medical community or based on publicly available information.

There is thus a need to provide a trustworthy system and method to provide information for evaluating professionals such as medical professionals based on merits and the medical professional's performance.

The Internet is a huge information repository. When individuals find themselves in need of an answer to a question within a specialized field of knowledge, such as health question, they often turn to the Internet. However, the sources of the answers to such questions provided on the Internet are often not identified and have dubious credibility. Accordingly, consulting the Internet with such questions, e.g., using a search engine, often leaves people more confused, scared and misinformed than they were before. There is a need to provide methods and systems to help people find reliable information in specialized fields such as medical and health-related fields.

However, seeking reliable answers in certain fields can be expensive, inefficient and inconvenient. For example, if one wants an answer for a curious, but not necessarily serious, ailment from a doctor, it can take weeks to get an appointment with the doctor. Also it is costly to visit the doctor or emergency room. While there is no replacement for an in-person visit with a doctor who knows your medical history, sometimes we may just need quick, reliable medical information or advice. Thus, there is a need for new systems and methods of communication and information exchange between doctors and patients (or investors and bankers; potential clients and lawyers; students and professors; and so on) beyond doctor office visits, such that patients can obtain quick, reliable medical information or advice from trustworthy doctors with very little cost, if any.

BRIEF SUMMARY

The following brief summary is not intended to include all features and aspects of the present invention, nor does it imply that the invention must include all features and aspects discussed in this summary. Some embodiments below describe interactions with doctors, but could apply to any professional providing medical diagnosis, treatment, advice, support or care.

The present disclosure, in some embodiments, provides computer-implemented methods and systems for evaluating healthcare professionals, comprising: a) receiving, by the computer processor, a plurality of attributes data indicative of professional qualification and performance; b) assigning each said attribute, by the computer processor, a value or a function calculating such a value based on the variables affecting that said attribute; c) computing and storing, by the computer processor, the sum of every result value of each attribute in step b; d) receiving, by the computer processor, feedback data for the healthcare professional's engagement with other users; e) assigning each feedback data, by the computer processor, a value or a function calculating such a value based on the variables affecting that said feedback data; f) computing and storing, by the computer processor, the sum of every result value of each feedback data in step e; g) generating, by the computer processor, an overall value based on step c and step f.

In one embodiment, the attributes indicative of professional qualification and performance are selected from a group of considerations comprising: education, training, certification, experience, publication, editorial positions, academic appointment, referrals, awards, professional society participation, and hospital affiliation. More specifically, the attributes indicatives of professional qualification and performance are selected from a group of considerations named as Education Factor, Training Factor, Certification Factor, Experience Factor, Publication Factor, Editorial Position Factor, Academic Appointment Factor, Referral Factor, Achievements and Awards Factor, Professional Society Participation Factor, Hospital Affiliation Factor, and the like. However, the above listed factors are not exhaustive, and other factors which contribute to the performance, reputation, or the practicing skills of the healthcare professional may be considered.

In another embodiment, the step of computing and storing the value of each attribute indicative of professional qualification and performance and computing the sum value of all attributes is achieved by a computer processor Profile Data Calculation Module. This module has already assigned each attribute individual value or functions to calculate such value based on variables affecting said attribute. This module will derive a sum of each individual value calculated under each attribute. Therefore, it is important to note that the value or the function to calculate such value assigned to each attribute should not be limited to the examples disclosed here. Various different points, numeric values or other forms of value may be assigned to each of the above attributes. Functions for each attribute may differ, to take into considerations of all the relevant variables that may affect the said attribute. The assigned value or the designed functions may differ from the examples explicitly set forth in this disclosure, and may be any assigned values or functions that reflect an evaluation of the healthcare professional's merits and overall standing.

In another embodiment, the step of computing and storing the value of each feedback or endorsement and sum the value of all the feedbacks and endorsements is processed by a computer processor Feedback Data Calculation Module. In addition, in the Feedback Data Calculation Module, the sum value of the feedback can be scaled by the contemporary nature of the feedback or endorsement. In this module, a value or a function to calculate such value is assigned to each feedback or endorsement activity. Based on the feedback or endorsement the healthcare professional received, this module will calculate a sum or a weighed sum of all the result values under each feedback or endorsement. Again, the value and function assigned to each feedback data should not be limited to the examples disclosed herein. Other such points, numeric value, or other forms of value or function to calculate such value may be assigned, and different functions may be formulated for weighting or otherwise valuing for each feedback data entry, taking into account any variables which may be relevant to the feedback data entry. Though the assigned value or the designed functions may be different than the examples in this disclosure, they reflect an evaluation of the healthcare professional's merits and overall standing and thus contemplated by the present disclosure.

The meaning of the sum of the Feedback Data value is scaled by the contemporary nature is that if the healthcare professional has been inactive for some time, the Feedback Data value will decay. Such decay can be a function of the days since the healthcare professional has not been active, or can be a function of the rate of the questions being answered out of the total questions sent to the healthcare professionals in certain period of time. A function may scale the sum raw Feedback Data points by the time consideration/contemporary nature of the data. Other functions may scale the sum raw Feedback Data Points by different factors or considerations. Such calculation should not be limited by the examples presented in this disclosure.

In one embodiment, the Profile Data Value and the Feedback Data Value are functions of their corresponding raw values respectively and are converted into a smaller range for easy understanding. For example, in one embodiment, the Profile Data value is converted into a numeric value range of 50-85. The Feedback Data value is converted to a range of 0-20. The overall value (Reputation Score) is converted into a range 50-100 (though a maximum 99 points of Reputation Score may be set). Such converting functions can be segmented linear functions of the corresponding raw data which may be designed to reflect a sharp drop in the first 30 days inactiveness. Other functions may convert the raw scores into a preferred value format, for example in numeric value or in percentile. One or more segmented linear functions may assign a different drop rate for the healthcare professional's inactiveness. The two components of the Reputation score (i.e., Profile Data Value and Feedback Data Value) may allocated differing weights under the teaching of the present disclosure.

In one embodiment, the present disclosure provides a system for generating a healthcare professional evaluation system, comprising a memory comprising instructions executable by one or more processors; and one or more processors coupled to the memory and operable to execute the instructions, the one or more processors being operable when executing the instructions to perform the steps of: a) receiving, by the computer processor, a plurality of attributes data indicative of professional qualification and performance; b) assigning each said attribute, by the computer processor, a value or a function calculating such a value based on the variables affecting that said attribute; c) computing and storing, by the computer processor, the sum of every result value of each attribute in step b; d) receiving, by the computer processor, feedback data for the healthcare professional's engagement with other users; e) assigning each feedback data, by the computer processor, a value or a function calculating such a value based on the variables affecting that said feedback data; f) computing and storing, by the computer processor, the sum of every result value of each feedback data in step e; g) generating, by the computer processor, an overall value based on step c and step f.

In one embodiment, the present disclosure provides one or more computer-readable storage media embodying software operable when executed by one or more computer systems to perform: a) receiving, by the computer processor, a plurality of attributes data indicative of professional qualification and performance; b) assigning each said attribute, by the computer processor, a value or a function calculating such a value based on the variables affecting that said attribute; c) computing and storing, by the computer processor, the sum of every result value of each attribute in step b; d) receiving, by the computer processor, feedback data for the healthcare professional's engagement with other users; e) assigning each feedback data, by the computer processor, a value or a function calculating such a value based on the variables affecting that said feedback data; f) computing and storing, by the computer processor, the sum of every result value of each feedback data in step e; g) generating, by the computer processor, an overall value based on step c and step f.

Such evaluation systems and methods are also applicable to institutions, other professionals in health industry and in clinic field, and institutions alike. Further, while some embodiments provided by the present disclosure are described primarily as involving healthcare professionals, the systems and methods provided herein may be advantageously employed for use by other professionals, including lawyers, teachers, accountants, contractors or any other service providers. The present disclosure describes interactions with doctors, but could apply to any professional providing medical diagnosis, treatment, advice or care. Further, while the present disclosure is described with particular respect to doctors, the present disclosure is not limited for use in any particular profession or area of expertise; rather, the systems and methods provided herein may be advantageously employed for use by other professionals or persons having expertise in any given field. For example, using the systems and methods provided herein, professionals in various fields may solicit and/or receive votes indicating skill in a particular specialty or sub-specialty, including, lawyers, professors, accountants, contractors, bankers and so on.

In one embodiment, the present disclosure provides a computer-implemented method of creating a computer-implemented method for evaluating a medical professional, the method comprising: generating, by the computer processor, categories of topics or practicing area the medical professional has expertise in; receiving a plurality of votes from both credentialed medical professional users and patient users under each topic or practicing area; computing and processing the votes from credentialed physicians and from the patient users separately under each topic or practicing area; and presenting the result value of the votes from credentialed physicians and from the patient users separately under each topic or practicing area.

In one embodiment, the computer-implemented method further comprises presenting content showing the medical professionals' credentials together with voting results.

In another embodiment, the present disclosure provides a system for generating a medical professional evaluation system, comprising a memory comprising instructions executable by one or more processors; and one or more processors coupled to the memory and operable to execute the instructions, the one or more processors being operable when executing the instructions to: generating, by the computer processor, categories of topics or practicing area the medical professional has expertise in; receiving a plurality of votes from both credentialed medical professional users and patient users under each topic or practicing area; computing and processing the votes from credentialed physicians and from the patient users separately under each topic or practicing area; and presenting the result value of the votes from credentialed physicians and from the patient users separately under each topic or practicing area.

In another embodiment, the present disclosure provides one or more computer-readable storage media embodying software operable when executed by one or more computer systems to perform: generating, by the computer processor, categories of topics or practicing area the medical professional has expertise in; receiving a plurality of votes from both credentialed medical professional users and patient users under each topic or practicing area; computing and processing the votes from credentialed physicians and from the patient users separately under each topic or practicing area; and presenting the result value of the votes from credentialed physicians and from the patient users separately under each topic or practicing area.

In yet another embodiment, the present disclosure provides computer-implemented systems and methods for providing quick and trustworthy answers to health information. In one embodiment, such computer-implemented system comprises steps of receiving, by the computer processor, a health related question from the users; placing the question in a queue where all unanswered questions are sequenced in reverse chronological order; delegating questions prioritized by their queue orders to verified healthcare professional users who are licensed with good standing; and displaying the answers provided by said verified healthcare professional users together with the question.

In one embodiment, the method of providing quick and trustworthy answers further comprises processing and associating the question with the topic tags or system ID to organize the questions based on content.

In another embodiment, the method of providing quick and trustworthy answers further comprises a step to present the user with existing similar questions in the system before the user submits the question.

In another embodiment, the method of providing quick and trustworthy answers further comprises delegating the questions only to the qualified healthcare professional with good standing.

In another embodiment, the healthcare professional users' files are completely transparent and viewable to other users. These healthcare professional users can be the healthcare professional users who provide answers or healthcare professional users who agree with the answers provided by others.

In another embodiment, the present disclosure provides a system for generating a system for providing quick and trustworthy answers to health information. In one embodiment, such computer-implemented system comprises steps of receiving, by the computer processor, a health related question from the users; placing the question in a queue where all unanswered questions are sequenced in reverse chronological order; delegating questions prioritized by their queue orders to verified healthcare professional users who are licensed with good standing; and displaying the answers provided by said verified healthcare professional users together with the question.

In another embodiment, the present invention provides one or more computer-readable storage media embodying software operable when executed by one or more computer systems to perform: receiving, by the computer processor, a health related question from the users; placing the question in a queue where all unanswered questions are sequenced in reverse chronological order; delegating questions prioritized by their queue orders to verified healthcare professional users who are licensed with good standing; and displaying the answers provided by said verified healthcare professional users together with the question.

In another embodiment, the present disclosure provides a computer-implemented method for facilitating virtual consultations between a patient and a healthcare professional, comprising the steps of: receiving, by a virtual consultation application hosted at least partially on a server, a request to initiate a virtual consultation from a patient using a patient computer device; receiving, by the virtual consultation application, information input by the patient relating to the patient's reason for the consultation; receiving, by the virtual consultation application, attachment information provided from the patient computer device; locating a healthcare professional available to provide a virtual consultation via a healthcare professional computer device accessing the virtual consultation application; and providing, by the virtual consultation application, a communications interface for virtual consultation between the patient and the healthcare professional, wherein the communications interface facilitates at least one of: video, audio and chat communications.

In yet another embodiment, the present disclosure provides a system for virtual healthcare consultations, the system including a virtual consultation application, hosted at least partially on a server and electronically accessible over at least one network system to at least one patient computer device and at least one healthcare professional computer device. The virtual consultation application is configured to: receive a request to initiate a virtual consultation from a patient using the at least one patient computer device; receive information input by the patient relating to the patient's reason for the consultation; receive attachment information provided from the patient computer device; locate a healthcare professional available to provide a virtual consultation via the at least one healthcare professional computer device accessing the virtual consultation application; and provide a communications interface for virtual consultation between the patient and the healthcare professional, wherein the communications interface facilitates at least one of: video, audio and chat communications.

In yet another embodiment, the present disclosure provides a non-transitory computer readable medium containing instructions for providing a method for facilitating virtual consultations between a patient and a healthcare professional enabled at least in part on a processor of a computerized device, wherein a virtual consultation application is electronically accessible by the processor and is hosted at least partially on a server and electronically accessible over at least one network system to at least one patient computer device and at least one healthcare professional computer device, the instructions, which when executed by the processor, performing the steps of: receiving, by the virtual consultation application, a request to initiate a virtual consultation from a patient using the at least one patient computer device; receiving, by the virtual consultation application, information input by the patient relating to the patient's reason for the consultation; receiving, by the virtual consultation application, attachment information provided from the patient computer device; locating a healthcare professional available to provide a virtual consultation via the at least one healthcare professional computer device accessing the virtual consultation application; and providing, by the virtual consultation application, a communications interface for virtual consultation between the patient and the healthcare professional, wherein the communications interface facilitates at least one of: video, audio and chat communications.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
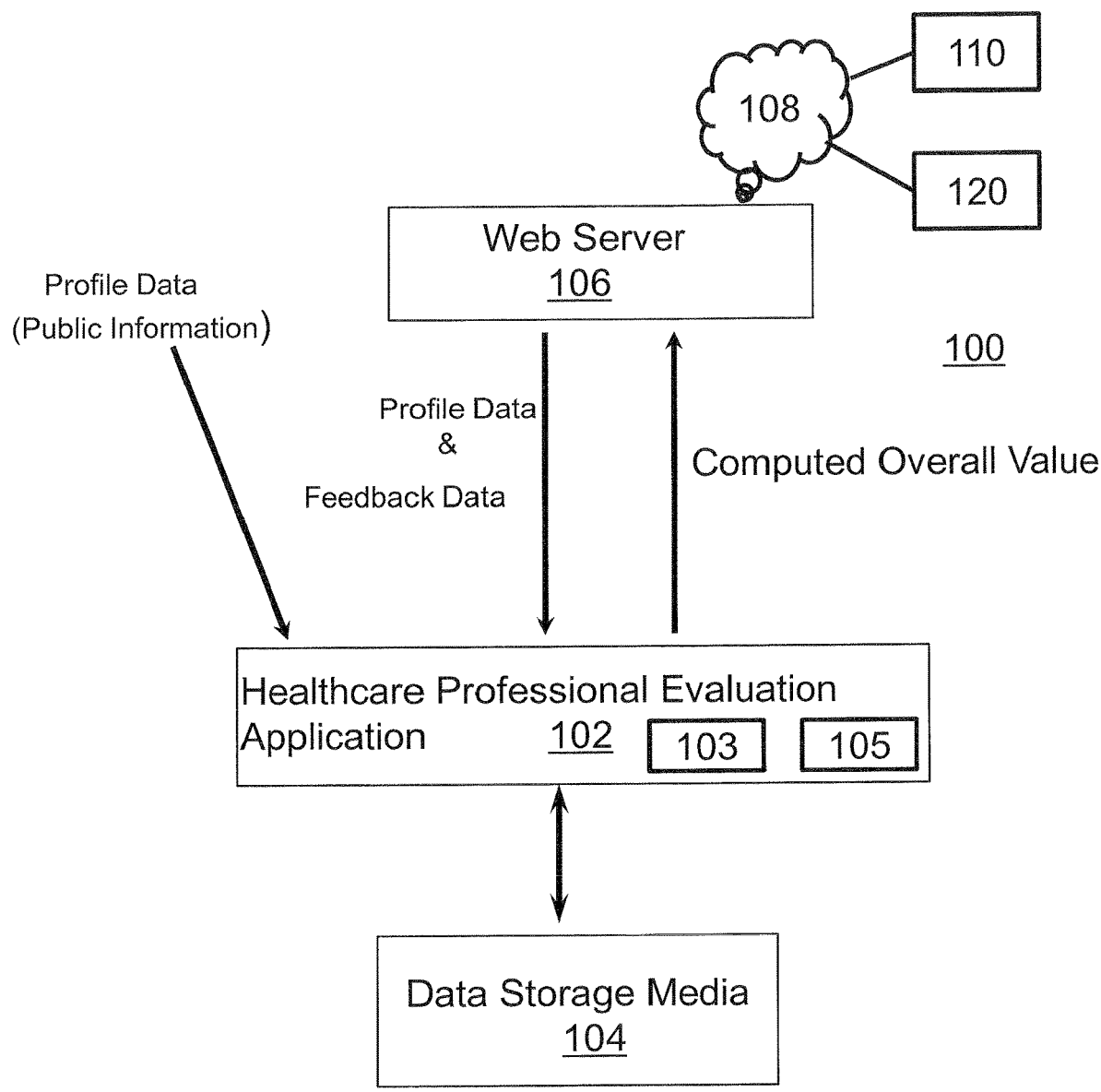
FIG. 1 is a schematic illustration of a healthcare professional evaluation system, in accordance with a first exemplary embodiment of the present disclosure.

In the following detailed description of the invention, numerous specific details are set forth in order to provide a more thorough understanding of the invention. However, one skilled in the art may practice the present invention with variation of the following details. In addition, some well-known features have not been described in detail in this description to avoid unnecessarily complicating the description.

Many embodiments of the disclosure may take the form of computer-executable instructions, including algorithms executed by a programmable computer. However, the disclosure can be practiced with other computer system configurations as well. Certain aspects of the disclosure can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

The disclosure also can be practiced in distributed computing environments, where tasks or modules are performed by remote processing devices that are linked through a communications network. Moreover, the disclosure can be practiced in Internet-based or cloud computing environments, where shared resources, software and information may be provided to computers and other devices on demand. In a distributed computing environment, program modules or subroutines may be located in both local and remote memory storage devices. Aspects of the disclosure described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks including the cloud. Data structures and transmissions of data particular to aspects of the disclosure are also encompassed within the scope of the disclosure.

While the present disclosure is described with particular respect to doctors and/or medical professionals, the present disclosure is not limited for use in any particular profession or area of expertise; rather, the systems and methods provided herein may be advantageously employed for use by other professionals or persons having particular expertise in any given field. For example, professionals in various fields may employ the systems and methods provided herein, including, lawyers, professors, accountants, contractors, bankers and so on The present invention provides systems and methods to evaluate healthcare professionals by assigning a healthcare professional an overall value (hereinafter referred to as "Reputation Score" for convenience and clarity, but such name does not limit the overall value to a numeric value). The system providing such a Reputation Score can be called "Healthcare Professional Evaluation System."

The Reputation Score has two components: Profile Data Value and Feedback Data Value. The Profile Data Value is computed based on information regarding a healthcare professional's merits (for example, the medical school, publications, years of experience, etc.). The Feedback Data Value is computed based on the feedback and endorsement the healthcare professional obtained from other healthcare professional users and/or patient users (for example, the answer to a health question provided by this healthcare professional is endorsed by other healthcare professionals).

The Reputation Score can be the sum of Profile Data Value and the Feedback Data Value. The Profile Data Value can be the raw Profile Data points or a converted value of the Profile Data points. The Feedback Data can be a weighed value of the raw Feedback Data points. The Reputation Score positively reflects each healthcare professional's overall standing based on merits and the recognition obtained from peers and patients. The Reputation Score gives patients a way to understand each healthcare professional's qualifications, knowledge of medical practices, and the quality of their engagement with patients or other medical professions. The patient users therefore can find and select professionals based on their trusted evaluations.

An important aspect of the present invention is that the present system or method is used to evaluate a healthcare professional who is certified or licensed in real life. All the healthcare professionals are presented in the social network in their real identity. The professional or practicing records can be obtained from public domain, as well as can be input by the healthcare professional himself/herself. Such professional or practicing records are accessible to all users and can be stored in the system or the server.

The Profile Data comprises a plurality of attributes indicative of professional qualification and performance. After receiving the Profile Data, the Profile Data Calculation module (which may include or be facilitated by a computer processor) recognizes the categories of the above profile data or information and assigns them to corresponding attributes (for example, the medical school information will be assigned to the attribute of Education Factor). The computer either assigns a value based on the information under certain attributes, or treats the information as variables of a predesigned function to calculate the value under certain attributes. Value obtained from all the attributes are added and the sum value is called Raw Profile Data Value.

In one embodiment, the attributes chosen to reflect professional qualification and performance comprise: Education Factor, Training Factor, Board Certification Factor, Experience Factor, Publication Factor, Editorial Position Factor, Academic Appointment Factor, Referral Factor, Achievements and Awards Factor, Board Discipline Factor, Conference Attendance Factor, Professional Society Participation Factor, Hospital Affiliation Factor, and the like. However, the above listed factors are not exhaustive. Persons skilled in the art can adjust the above factors by either adding new factors which they believe contribute to the performance, reputation and the practicing skills of the physician, or deleting some factors if such factors are considered less relevant.

The second component of the Reputation Score is Feedback Data Value. Raw Feedback Data value is obtained based on the feedback information of an individual healthcare professional's engagement with other users of the system (e.g., other healthcare professionals or patients users). Such feedbacks are quantified by the computer processor. Such feedbacks may be provided from the patient users or from peer healthcare professional users. In one embodiment, the feedback information from the patient users comprise: being followed by a patient in a social network, being recommended by a patient user, being added by a patient as the patient's physician, being thanked by a patient for an answer to a health related question, or such answer being shared by the patient with friends by Email, SMS, push notification, or on third party social network (e.g., Facebook or Twitter), being requested by the patient to make an appointment (for a doctor office visit), being voted by a patient for having knowledge relevant to a specific topic.

The feedbacks or recognitions obtained from other peer healthcare professional users may be given more weight and can be assigned a higher value than for feedback obtained from patients. For example, if other healthcare professionals send a message to a healthcare professional, other healthcare professionals refer the healthcare professional's answer to other users or refer a question to the healthcare professional, other healthcare professionals add the healthcare professional to his or her own network, other healthcare professionals agree with answers created by the healthcare professional, or other healthcare professionals recommended the healthcare professional on the network, higher value points will be allocated to the healthcare professional. Values derived from the feedback and endorsement stated above are added together counted toward the Reputation Score as a second component, Feedback Data value.

Again, the feedbacks and endorsements listed above are not exhaustive. Persons skilled in the art can either add more feedback and endorsement data when they believe such feedback contributes to the performance, knowledge, credibility or practicing skills of the healthcare professionals. Or they can delete some of the above listed feedback data entries for being less relevant.

The raw Feedback Data Value can be a sum of the values assigned to each countable activity reflecting the value of the healthcare professional's engagement. Or such value can be calculated from functions assigned to the countable activity based on variables that affect such countable activity. The value or the function assigned to each feedback are not limited to the examples provided in the embodiments. Persons skilled in the art can assign different value to each feedback data entry. Persons skilled in the art can also design different functions to calculate the value of each feedback since they may believe certain variables should be given different weight, or other variables should be added to such a function to compute the value of the said feedback data. Even though such modified calculation may result different sum value, they are nonetheless covered by this invention because these calculations all reflect similar evaluation/consideration of the feedback or endorsement on the healthcare professional's engagement with other healthcare professionals and patients.

However, the value derived from the feedback data is not static. It will decrease with inactivity. To avoid a decrease, the healthcare professional must engage in the activities at a rate earning more points than the minimum participation points required. The healthcare professional can also restore value derived from the feedback by reengagement. Therefore, the second component of the Reputation Score, the raw feedback data value is scaled by contemporary nature. It reflects the current feedback of the healthcare professional's present knowledge.

Both the Profile Data and the Feedback Data Value can be converted into a smaller range numeric value for easy understanding. In one embodiment, the Profile Data is set within range 50-85, and the Feedback Data value is set within range 0-20. The conversion functions for Profile Data and Feedback Data can be different segmented linear functions of their respective raw data. Thus, the Reputation Score can be calculated to a range 0-100. However, the system can set a maximum value for the Reputation Score. For example, in one example, the maximum value of Reputation Score is 99.

FIG. 1 is a schematic illustration of a healthcare professional evaluation system 100 (which may be referred to hereinafter as 'system 100'), in accordance with a first exemplary embodiment of the present disclosure. As shown in FIG. 1, the system includes multiple components such as a web server 106, a Healthcare professional evaluation application 102, and a data storage media 104. These components are described below and may be located on the same device (e.g., a server, mainframe, desktop Personal Computer (PC), laptop, mobile device (smart phone or tablet), Personal Digital Assistant (PDA), telephone, mobile phone kiosk, cable box, and an other device) or may be located on separate devices connected by a net work (e.g., the internet, or the cloud infrastructure), with wired and/or wireless segments. Those skilled in the art will appreciate that there may be more than one data storage media 104 and healthcare professional evaluation application 102 running on a device.

The healthcare professional evaluation application 102 may be fully or partially hosted on the server 106, and electronically accessible over at least one network system 108. The network system 108 may include any type of network infrastructure, such as the Internet, or any other wired, wireless and/or partially wired network. The server 106, application 102 and network system 108 may include a variety of hardware and software components to provide successful functioning of the server 106 and the application 102, as is well-known within the art. Further, any features, characteristics, designs and/or functions that are known within the art may be included with the system 100 to further enhance its efficiency. The application 102 may include any computer-readable memory or databases, which may be stored in any computer-readable medium, and may be accessible by a computer processor. The application 102 may further include or access computer program instructions which may cause a processor to perform any algorithms and/or functions described in this disclosure. The healthcare professional evaluation application 102 may include or have access to a Profile Data Calculation Module 103 and a Feedback Data Calculation Module 105.

The system may further include one or more patient computer devices 110 and one or more healthcare professional computer devices 120. The patient computer devices 110 and healthcare professional computer devices 120 may be any computerized devices capable of communicating with the application 102, for example via a network system 108. The one or more patient computer device 110 may be operated by a patient user of the system 100, and the one or more healthcare professional computer devices 120 may be operated by any healthcare professional (or other professional), such as a primary care physician, medical doctor, nurse, medical staff or other medical professional, or any representative thereof.

The data storage media 104 is a computer-readable storage medium, which may be any device or medium that can store code and/or data for use by a computer system. This includes, but not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed. The data storage media 104 may store healthcare professionals' profile information which may be included and accessible for display to users within the system 100 as webpage profiles for the healthcare professionals.

As shown in FIG. 1, data for the healthcare professional evaluation system 100 may be provided from public domain, third party, existing database and stored data on the web server 106. Users of patient devices 110 and users of healthcare professional devices 120 may further input data for use by the system 100. After the Healthcare Professional Evaluation Application 102 receives these data, it will process such data and produce a value based on the data. Such value can be numeric, in percentage, or in other form. Any form may be utilized to present such value.

Figure 2:
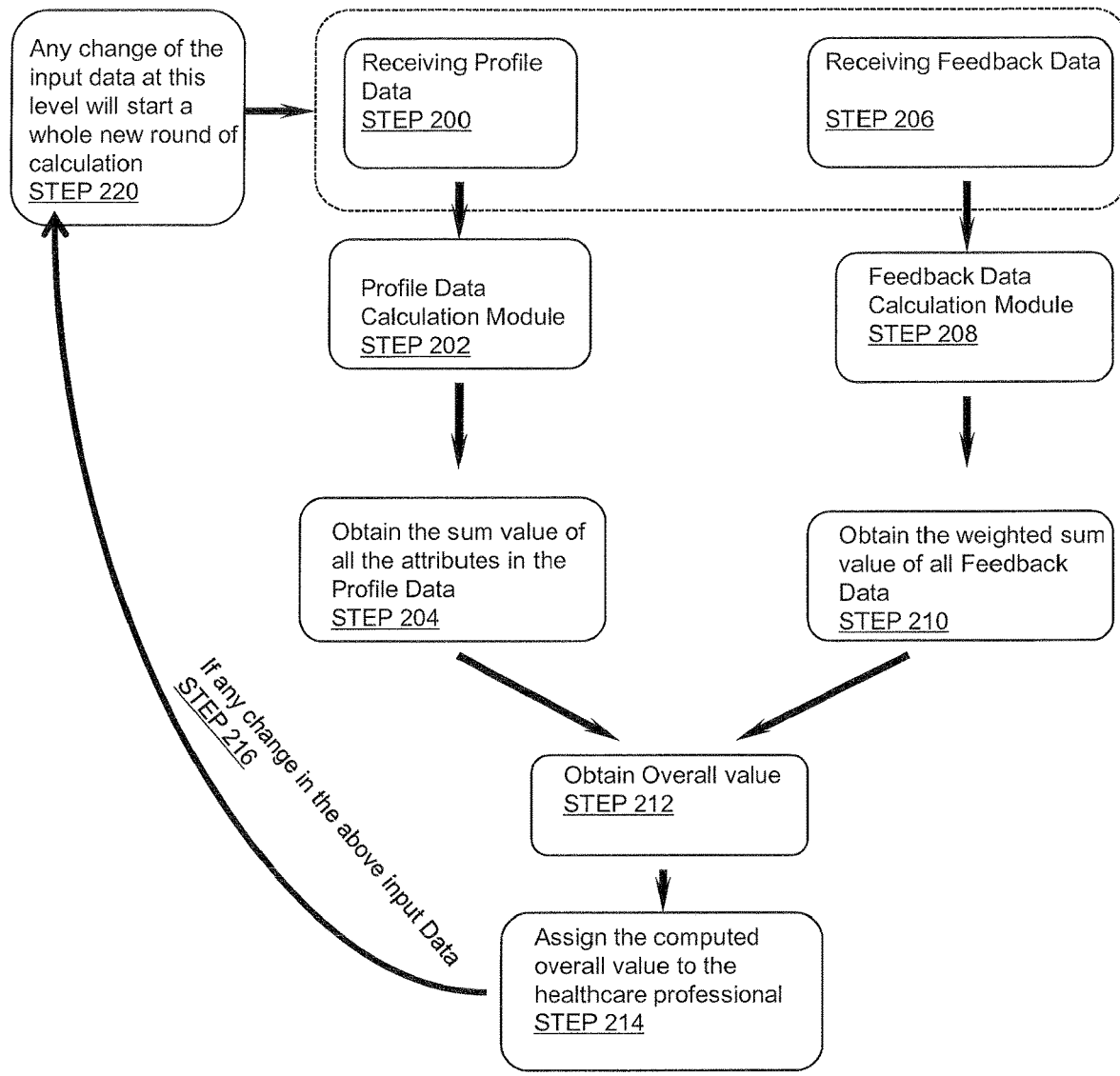
FIG. 2 is a flowchart illustrating a method for evaluating a healthcare professional, in accordance with the first exemplary embodiment of the disclosure.

FIG. 2 is a flowchart illustrating a method for evaluating a healthcare professional, in accordance with the first exemplary embodiment of the present disclosure. The method may be performed or facilitated using the Healthcare Professional Evaluation System 100 shown in FIG. 1. The application 102 receives profile data either from public domain data (which may be referred to herein as "third party data element") or from the healthcare professional's own input (e.g., using healthcare professional device 120). The application 102 receives the feedback or endorsement data regarding the healthcare professional's activities through patient devices 110, healthcare professional devices 120 (e.g., as input to the application 102 through the webserver 106).

The Profile Data of a plurality of attributes indicative of professional qualification and performance are processed by the Profile Data Calculation Module 103 (STEP 202). The Profile Data Value can be a sum value (STEP 204) derived from the factors related to professional qualification and performance. For example, factors taken into consideration can include: Education Factor, Training Factor, Board Certification Factor, Experience Factor, Publication Factor, Editorial Position Factor, Academic Appointment Factor, Referral Factor, Achievements and Awards Factor, Board Discipline Record Factor, Conference Attendance Factor, Professional Society Participation Factor, Hospital Affiliation Factor and so on. Different weights and/or values are assigned to these factors and the sum of all the result values of each factor constitutes the Raw Profile Data Value. However, these factors are not an exhaustive list, and many other factors may be considered when such factors contribute to or are indicative of the performance or reputation and the practicing skills of the healthcare professional.

In addition, the value or the function assigned to each factor are not limited to the examples presented in the embodiments. Persons skilled in the art will readily understand that different values may be assigned to each feedback data and associated factors or attributes. As such, functions to calculate the value of each attribute as provided herein may be adjusted such that different variables or factors are given different weight, or other variables are added to such a function to compute the said attribute. Even though such modified calculation may result in a different sum value, they are nonetheless contemplated by the present disclosure, as such calculations rely on the evaluation methods of the healthcare professional's merits as provided herein.

In one embodiment, the Education Factor is a function of the ranking of the medical school the healthcare professional graduated from. The function can take into consideration the school's clinical ranking and the research ranking. Every medical school the healthcare professional has attended contributes to this factor. The school's clinical ranking and research ranking can be obtained from public information available via the internet or provided by third party data, or may exist in a database on the web server 106 or data storage media 104 of the system 100, as long as the ranking is reputable and is applied consistently to all the healthcare professionals. However, persons skilled in the art will readily understand from the present disclosure that other variables which contribute to the medical school's reputation may be included to modify the functions presented herein (e.g., the publications of the school's faculty) and thus affect the result value of the Education Factor. Also, the healthcare professional's academic performance during his/her study can be a variable affecting the result value of the Education Factor as well.

In one embodiment, the Training Factor is a function of the ranking of the residency hospital and the degree the healthcare professional obtained (for example, if the medical profession obtained a Doctorate in addition to MD or DO or MBBS or DDS or DMD, more points will be allocated). Again, some other factors can be taken into consideration and become variables of the function as long as such factors affect the reputation of the residency program or the credibility of the degree.

In one embodiment, the Board Certification Factor is a sum value of each Board Certificate the healthcare professional has obtained. Either a fixed value or a function can be assigned to each Board Certification record. Factors like how long ago the healthcare professional obtained such certificate can affect the value of the Board Certification Factor.

In one embodiment, the Experience Factor is a function of the years the healthcare professional has been practicing. Therefore, facts like that the healthcare professional has suspended his practice for a period of time can be taken into consideration and be a variable in a function. A maximum value can be set to avoid overweighing this (or any other) factor.

In one embodiment, the Publication Factor is a function of the reputation of the journals or periodicals where the healthcare professional published his work. The variables included in such a function can be the ranking of the journals or periodicals and the numbers of articles the healthcare professional has published. Such publications can be obtained either from public domain, or input by the healthcare professional himself. For the healthcare professional input information, the PubMed identifier or similar identifier of the publication may be required.

In one embodiment, the Editorial Position Factor is a function of the ranking of the Journal where the healthcare professional serves as an editor and the level of the editorial position the healthcare professional has been serving. For example, if a medical professional has been an editor or associate editor of a PubMed-indexed journal, he will obtain a higher value in Editorial Position Factor than serving on an advisory board, or be a reviewer at such a journal.

In one embodiment, the Academic Appointment Factor is a function of the level of the academic appointment position the medical profession has taken and the rank of the institution the healthcare professional serves his appointment. The higher level, for example, being a Chair of a Department at a top medical school will earn the medical professional a much higher value.

In one embodiment, the Referral Information Factor is a function of the number of times the healthcare professional is referred and the qualification of the other healthcare professionals who referred this healthcare professional. This information can be obtained from public domain and/or from the server 106 (e.g., as referral information may be input to the system 100 by referring healthcare professionals using healthcare professional devices 120 and accessible by the server 106).

In one embodiment, the Achievements and Awards Factor is a function of the credibility of each achievement and award. The variables can include: how well the award is recognized by peers, the recency of the award, the number of the awards the healthcare professional has obtained. Sometimes, a predetermined value can be assigned to each achievement or award. Therefore, the Achievements and Awards Factor can simply be a sum value of points assigned to each award the healthcare professional achieved. For example, if the healthcare professional has been listed in a selected doctor directory, a predetermined value will be added toward the Achievements and Awards Factor. Or if the healthcare professional has been awarded the best doctor in 2013 in a city or town, a higher predetermined value may be added toward the Achievements and Awards Factor.

In one embodiment, the Professional Society Participation Factor is a function of the credibility of each society the healthcare professional has joined. The variables can include: how reputable the professional society is viewed among peers, the size of such professional society, and the number of the professional societies the healthcare professional has joined.

In one embodiment, the Hospital Affiliation Factor is a function of the ranking of the hospital and number of the hospitals the healthcare professional has been affiliated with. Such hospital's ranking can be found in public domain as long as the ranking is reputable and consistently applied on each healthcare professional.

Other such factors and profile data relevant to attributes indicative of a healthcare professional's qualifications and performance may be included in the formulations provided herein for obtaining a value reflective of a healthcare professional's overall merits and standing.

In one embodiment, the Profile Data Calculation Module 103 includes an authentication tool which allows the healthcare professional to authenticate his/her own profile data, and such authentication can be reflected in the Profile Data Value. For example, a multiplier (for example, 1.1-1.8) can be assigned to the value of each attribute validated or verified by the healthcare professional himself. Alternatively, certain points can be allocated to the healthcare professional if the healthcare professional validates the profile data.

The Feedback Data derived from feedback or endorsement reflects recognition and evaluation from peer healthcare professionals and patients. It also reflects how appreciative the community has been of their advice. The Feedback Data is processed by Feedback Data Calculation Module 105 (STEP 208). In one embodiment, the Feedback Data Value is calculated as follows:

$$\text{Feedback Data Value} = \text{Raw Feedback Data Points} * \text{Time Factor.}$$

The Feedback Data Value indicates the quality, quantity, and recency of the healthcare professional's engagement with other healthcare professionals and patients. Raw Feedback Data increases incrementally with each new unit of engagement that indicates quality. For example, if the healthcare professional provides an answer to a question asked by a patient and the patient shows appreciation (e.g., by sending appreciation message, or by recommending the answer to other people), points or value will be allocated to the healthcare professional. Further, if this answer is recognized by other peer healthcare professional, more points will be allocated to the answer provider.

More specifically, a value or a function may be assigned to each of the feedback data which may then be summed, resulting in a value for raw Feedback Data Points. For example, the feedback data may include: the number of times a healthcare professional is "followed" within the system 100 by other patient users or other healthcare professional users, the number of recommendations the healthcare professional obtained from patients or healthcare professional users, the number of times being added as other patient users' own healthcare provider (e.g., physician), the number of office visit appointments the healthcare professional obtained through the system 100, the number of votes from other users for knowing a specific topic, the number of thanks from patient users of the system 100 the healthcare professional obtained for answering a question or providing some medical issue related content, the number of times the answer provided by the healthcare professional is shared by patients or other healthcare professional users with others outside of the system 100, for example, by Email or through third party social networks (e.g., Facebook or Twitter). Answers provided by healthcare professionals in the system 100 may be shareable with such outside users through any known technique, including for example, by embedding tools in the pages displaying answers for emailing, republishing and sharing via social networks (e.g., "email this answer," share on Facebook, "Like" on Facebook, "Tweet" the answer on Twitter, etc.).

However, the recognition obtained from other peer healthcare professionals (e.g., doctors) may be given a higher value than for feedback obtained from patients. For example, if other healthcare professionals send a message to a healthcare professional to ask questions, other healthcare professionals referred the healthcare professional's answer to other users or refer a question to the healthcare professional, other healthcare professionals added the healthcare professional to their own network (e.g., by "following," or adding to their network of healthcare professionals on the system 100), other healthcare professionals agree with the healthcare professional's answer, or other healthcare professionals recommend the healthcare professional on the system 100, a higher value can be assigned to the healthcare professional. This list is not exhaustive. Other such feedback or endorsement reflecting the quality of the healthcare professional's activities may be considered and included in the computation of Feedback Data Value.

Updating profile by the healthcare professional can add value to the feedback data as well. However, this engagement is not recognition from others. Nonetheless, such an action can be given a value and count toward the Feedback Data Value to encourage a healthcare professional to update his file and to improve the communication between the healthcare professionals and the patients.

However, in one of the embodiment, the Raw Feedback Data will decrease with inactivity. In such a case, the final Feedback Data may be obtained by multiplying Raw Feedback Data with a Time Factor. In this way, the Feedback Data can reflect the current knowledge or responsiveness of the healthcare professional. A rate of fall can be set and a minimum participation points per day can be set to make the Feedback Data Value maintainable. If a healthcare professional keeps inactive for a certain period of time, the Feedback Data will decrease, which will lead the overall Reputation Score decrease. In order to avoid a decrease of the score, the healthcare professional must engage activities within the system 100 with other peer healthcare professional and patient users at a rate earning more points than the minimum participation points required for each day.

If the healthcare professional user remains current on the system 100, then all previous content decays at a steady slow rate that is more than offset by ongoing activity. When the healthcare professional user becomes inactive, a more rapid, reversible decay in the value occurs-this decay is reversed when the physician re-engaged and generates more points through activity on the site. The time decay for inactivity can be set for a sudden drop for the first short period of time, then less value will be lost gradually over the following longer period of time. The physician can restore the score by re-engagement.

After the Profile Data Calculation Module 103 and Feedback Data Calculation Module 105 compute the Profile Data Value and the Feedback Data Value (Raw Feedback Data Value*Time Factor), an overall value, also referred to as Reputation Score, is obtained (STEP 212). If any data entry changes, the system/computer processor will detect the change and recalculate the Reputation Score from the beginning (STEPS 216, 220). Before the next change is detected, the Reputation Score is assigned to the healthcare professional (STEP 214).

Those skilled in the art, having benefit of this detailed description, will appreciate that there will be many other uses for the physician evaluation system, and that the evaluation system may be applied to evaluate either other medical entities or other professional services (e.g., medical institutions, lawyers, and so forth.)

Definitions

The term "social network" is used herein to refer to any computing system that allows users to communicate or otherwise interact with each other. The healthcare professional evaluation system 100 provided herein is a social network. For example, such network can provide a platform for the communication and interaction between patient users and healthcare professionals. The patient users can ask questions and obtain answers from qualified healthcare professionals. The healthcare professionals can ask questions as well and obtain answers from other peer qualified healthcare professionals. The patient users can upload their personal health information documents and share them with designated healthcare professionals. The patient can also make doctor visit appointments with designated healthcare professionals through the system 100. In addition, the interaction between the patient users and the healthcare professionals can be in any form carried out by the system 100. For example, the patient users can send "thank you" note for answers provided by the healthcare professionals, the healthcare professionals can show "agree" to answers provided by other peer healthcare professionals. The ways of communication and interaction are not limited to the examples explicitly listed in the present disclosure.

The term "profile" is used herein to refer to a user's profile containing pages and/or information visible to the public generally, information that is visible only to the user herself, information visible only to users specified by the user, information visible as specified by the user, and information that may not be visible to other users. In one embodiment, in healthcare professionals' profiles, the information regarding professional and practicing records are open to all users. The users can learn a healthcare professional's expertise and experience by viewing the content in the healthcare professional's profile. In a healthcare professional's profile, a user can find not only the registration and license information, but also information like the expertise, the geographic location, the publication, and even the answers to health related questions the healthcare professional has provided before. To the contrary, a patient user's profile can choose to be private and not viewable to other users. Only with the permission from the patient user, a healthcare professional can access the patient user's health information or the medical documents the patient uploaded.

Other factors or variables not specifically cited or referenced in the present disclosure may also be included in the functions provided herein without limiting the scope of the claimed invention. Accordingly, other factors or variables may be further used to be part of the function to evaluate the healthcare professionals. It should further be noted that the present disclosure contemplates that weights indicated in association with the various factors or variables may also be adjusted as additional factors are added or as necessary to provide a more accurate evaluation.

The term "patient," "patient user" or the like is used herein in a broad meaning to refer to any person or any entity seeking health information utilizing the systems provided herein. The patient can ask questions regarding any aspect of healthcare. Any patient can be the user of a social network.

The term "healthcare professional" is used herein to refer to any medical practitioner providing healthcare services of any kind, or any kind of services appurtenant to healthcare. The healthcare professionals include any doctor, group practice, and/or any professional providing or capable of providing healthcare services While the present disclosure presents exemplary embodiments with specific reference to "healthcare professionals" and "patients," the present invention is not so limited; the systems and methods herein may be employed by various other professionals and potential users/clients, including lawyers/clients, teachers/students, accountants/clients, contractors or any other service providers and recipients thereof.

The term "doctor" is used herein in its broadest meaning to refer to any medical practitioner or healthcare professional providing healthcare services of any kind, or any kind of services appurtenant to healthcare. The plural form of doctors includes any doctor, group practice, any professional other than a physician providing or capable of providing healthcare services. Such a doctor can be a dentist, an optometrist, a therapist, a chiropractor, and anyone else who provides healthcare services to the user within the medical field.

The term "overall value" is used herein to refer to a value generated by a computer processor based on the healthcare professional's professional achievements, qualifications and performance (i.e., Profile Data), and feedback and endorsement (i.e., Feedback Data) the healthcare professional received in the system 100. For convenience, sometimes the overall value is also called "Reputation Score" without limiting the scope or meaning of the overall value to any specific formality. The overall value can be presented in numeric value, or in other preferred form, such as percentile, letters, words, symbols, icons or the like. The overall value can be based on a sum of the raw value of Profile Data and the raw value of Feedback Data. The overall value can also be converted to a smaller numeric value (or any other form) for presentation to users and ease of understanding. The overall value can be a segmented function to the raw value of Profile Data and of Feedback or Endorsement Data, separately or collectively.

The term "Feedback Data Value" is used herein to refer to a weighed sum value of all countable feedback or endorsement data (see FIG. 2, STEP 208). The accumulation is based on the feedback or the endorsement the healthcare professional received in the system 100. The Feedback Data Value decays slowly in the absence of new contributions.

The term "attributes indicative of professional qualification and performance" is used herein to refer any consideration that contributes to the healthcare professional's performance in the healthcare field and is included in Profile Data. It may include, but is not limited to, board certification, education, practicing experience, publications, referral information, training, editorial positions, academic appointments, awards, professional society participation, board discipline record, the involvement in malpractice litigation, affiliation to a hospital, and other achievements and awards considerations. This term is not limited to the attributes listed above or in the embodiments. Persons skilled in the art will readily understand that other such considerations may contribute to the healthcare professional's qualification and professional performance and thus may be included in Profile Data.

The term "third party" is used herein to include a patient, an insurance company, a healthcare organization, a professional organization, a government, and any organization that collects or provides access to healthcare-related information.

The scope of the invention is not limited to any of these definitions or to specific examples mentioned therein, but is intended to include the most general concepts embodied by these and other terms.

EXAMPLE

Evaluating a Healthcare Provider by Providing a Reputation Score

This example illustrates systems and methods to evaluate a healthcare provider (e.g., a doctor) by assigning the healthcare provider a Reputation Score (in numeric value) based on the healthcare provider's professional achievements and the engagement recognized by patients and other peer healthcare providers. However, the following embodiment is only an exemplified application of the present invention, the described systems and methods below are completely applicable to other professionals and/or service providers. The Reputation Score represents a healthcare provider's overall standing, based on merits and feedback from other healthcare providers and patient users. The Reputation Score has two components: Profile Data Value and Feedback Data Value. The Reputation Score can be calculated as follows:

Reputation Score=Profile Data Value+Feedback Data Value

The above Reputation Score can be obtained by either summing the raw Profile Data Value and raw Feedback Data Value. Or, the Reputation Score can be a sum of weighed Profile Data Value and weighted Feedback Data Value. The weighted Profile Data Value and weighted Feedback Data Value can each be obtained through a segmented linear function of the corresponding raw Profile Data Value and raw Feedback Data Value respectively. In this example, the segmented linear function is designed to give the initial contributions (i.e., initial activity/interaction in the system 100 by healthcare professionals) more weight to encourage the healthcare professionals' engagement. Once the Reputation Score reaches a certain predetermined level (e.g., a score of "70" out of a possible 99), the healthcare professional must increasingly engage in activities on the system 100 in order to gain successive points of the Reputation Score.

I. Conversion of Raw Profile Data Points to Profile Data Value and the Raw Feedback Data Points to Feedback Data Value In this example, the Reputation Score is set to be in a range of 50-100 for easy understanding when provided to users. Within this rage, the Profile Data Value is set to contribute about 50-85 points, and the Feedback Data Value is set to contribute about 0-20 points. The functions for converting both Profile Data Value and the Feedback Data Value are not pure linear functions, but segmented linear functions. These converting functions are designed in a way that the initial accumulation of the points takes less effort than later phases. This approach will encourage the initial involvement of the healthcare professional users. However, as described below, when the Profile Data Value and Feedback Data Value are close to their full value, more efforts and contribution needed to bring the healthcare professional users to be among the best healthcare professional users (e.g., having the highest Reputation Score).

The Reputation Score may be limited by a maximum value. For example, the sum of the raw Profile Data Points and the raw Feedback Points may have a value which would produce a corresponding converted Reputation Score that would exceed the maximum Reputation Score; however, if such maximum Reputation Score value is set, the following formula can be used to set up the maximum of the Reputation Score (e.g., limiting the Reputation Score to a maximum of 99 points):

Reputation Score=Min(Profile Data Value+Feedback Data Value,99)

The above mentioned functions converting the raw values to the weighted values are not pure linear functions, but segmented linear functions, such that in each successive segment, proportionate increases in converted value (i.e., Profile Data Value or Feedback Data Value) require successively greater increases in raw values (i.e., raw Profile Data Value and raw Feedback Data Value). For example, a first linear segment may correspond with a range of converted value from 55 to 60 and may require an increase of raw values (x) to produce an increase of one point converted value (e.g., from 55 to 56, 56 to 57, and so on up to 60). In a second linear segment (e.g., corresponding with a range of converted value from 60 to 70), increasing one point of converted value (e.g., from 60 to 61, 61 to 62, and so on up to 70) may require some multiple of x (A*x, where A>1), such as one and one-half times the increase of raw values (1.5x) as required within the first segment. Similarly, increasing one point of converted value in a third linear segment (e.g., corresponding with a range of converted value from 70 to 80) may require an even greater multiple of x (B*x, where B>A), such as three times the increase of raw values (3x) as required within the first segment. Any number of linear segments, each corresponding to ranges of converted values, may be included.

Thus, the initial contributions (e.g., as supplied by a healthcare professional's initial interactivity within the system 100) may be weighted highest. For example, to obtain the first points of the converted Reputation Score (e.g., starting from 50 and increasing to 55), the healthcare profession may needs only a small increase (e.g., 150 points) in raw score. The first few answers provided by the healthcare profession in the system 100 causes a rapid climb in Reputation Score. The climb in later segments (e.g., from 70 to 90) of the Reputation Score may require a modest effort by the healthcare professional to engage in activity on the system 100 (e.g., calibrated to about a month of substantial engagement). The highest scores (e.g., scores above 90) become progressively more difficult to achieve, and may require significant effort over a prolonged period of time in engaging in activity on the system 100—a rise in converted Reputation Score from 95 to 99, for example, may require an increase of 800,000 points of the Raw Reputation Score.

The Raw Profile Data Points and the Raw Feedback Data Points may be converted separately into Profile Data Value and Feedback Data Value. Then the converted scores are added together to obtain the Reputation Score.

II. Calculation of Raw Profile Data Value

Since much of the healthcare professionals' qualification information is public, the Profile Data can be obtained from the public domain (also called "third party" data element). Such information can be accessed and/or stored in the system 100 and to be used match with the Profile Data information input by the healthcare professional. The Raw Profile Data Value is a sum of values calculated under each attribute indicative of professional qualification and performance. For example, such attributes can include: Education Factor, Training Factor, Board Certification Factor, Experience Factor, Publication Factor, Editorial Position Factor, Academic Appointment Factor, Referral Factor, Achievements and Awards Factor, Professional Society Participation Factor, Hospital Affiliation Factor. Different values and functions calculating such values are assigned to these factors and the sum of these points constitute the Raw Profile Data Score. However, the above listed factors is not a exhaustive list, many other factors may be considered when such factors contribute to the performance or reputation and the practicing skills of the healthcare professional, for example, board discipline record, conference attendance and other such factors. A numeric value can be given to some of the above factors and be added to the Raw Profile Data Value. Persons skilled in the art can assign different numeric values to each of the above factors to obtain a different sum value, but reflects similar evaluation/consideration of the healthcare professional's merits.

In addition, different functions may be implemented to calculate the value of each attribute, as it may be desirable to include certain variables and weight them differently. Even though such modified calculation may result different sum value, they are nonetheless covered by this invention because these calculations all reflect similar evaluation/consideration of the healthcare professional's merits.

A healthcare professional may verify the Profile Data in the system 100, for example, by signing into the healthcare professional's account in the system 100 using healthcare professional computer device 120. By verifying the third party element information, the healthcare professional can obtain an increased value or weight (e.g., 10%) assigned to each third party data element that has been verified as valid by himself:

Raw Profile Data Score(for a doctor registered in the network)=(1.1)*Raw Profile Data Score generated by the system before verification The overall Raw Profile Data Value is a sum of the points calculated and added by the computer processor under each of the following parameters:

Raw Profile Data Score=$f$(Education Factor)+$f$(Training Factor)+$f$(Board Certification Factor)+$f$(Experience Factor)+$f$(Publication Factor)+$f$(Editorial Position Factor)+$f$(Academic Appointment Factor)+$f$(Referral Factor)+$f$(Achievements and Awards Factor)+$f$(Professional Society Participation Factor)+$f$(Hospital Affiliation Factor).

1. The Education Factor:

In this example, the Education Factor is a function of the clinical ranking and the research ranking of the medical school the healthcare professional graduated from. Every medical school the healthcare professional has attended will contribute to this factor. The school's clinical ranking and research ranking can be obtained from internet, third party, or existing database on the web server 106 of the system 100, as long as the ranking is reputable and is applied consistently to all the healthcare professionals. The Education Factor can be calculated by the following formula:

$$\text{Education Factor} = [(A-\text{clinical rank})*B + (A-\text{research rank})*C]_{School\ 1} + \ldots + [(A-\text{clinical rank})*B + (A-\text{research rank})*C]_{School\ n}$$

where, A=the number of ranked schools, or may be set to any fixed value,

B=a fixed weighting factor for the clinical ranking component of the Education Factor, and C=a weight factor for the research ranking component of the Education Factor.

A maximum number of points can be set to adjust the weight of the Education factor, or any other factor, in the overall Profile Data Value.

2. Training Factor:

In this example, the Training Factor is obtained by assigning value to each residency, fellowship and degree that the doctor completed. The Training Factor is determined by the following formula:

$$\text{Training Factor} = \text{completion of a residency}(x\ \text{points}) + \text{completion of a fellowship}(y\ \text{points}) + \text{completion a Doctorate in addition to MD or DO or MBBS or DDS or DMD}(z\ \text{points}).$$

The values assigned to the various components of this factor (e.g., x, y and z) may be adjusted to give different weight to different degrees and obtain a value similarly reflected the training the healthcare professional obtained.

3. Board Certification Factor:

The Board Certification Factor can be a sum value of each Board Certificate the healthcare professional has obtained. Either a fixed value or a function can be assigned to each Board Certification record. Factors like how long ago the healthcare professional obtained such certificate can affect the value of the Board Certification Factor. In one example, if the healthcare professional obtained Board Certification from American Board of Medical Specialties (ABMS) or American Optometric Association (AOA) specialty, a specific number of points will be allocated. With specialty certification, for each additional certification, additional points will be given.

4. Experience Factor:

In this example, the Experience Factor is determined by years since the healthcare professional graduated from medical school, or by years of active practice. The formula is as follows:

$$\text{Experience Factor} = \text{Annual experience points} * \text{years since graduation}$$

This factor can be assigned a maximum value to adjust its weight counting toward Personal Profile Data.

5. Publication Factor:

In this example, the Publication Factor is determined as follows:

$$\text{Publication Factor} = u\ \text{points} * \text{number of Peer-reviewed publications} + v\ \text{points} * \text{number of additional publication}$$

A maximum value may be set for the Publication Factor. When the publication is entered by the healthcare professional, a PMID may be required (PubMed identifier or PubMed unique identifier). The system 100 will update the publications of the healthcare professional by frequently obtaining updates from public accessible publication database.

6. Editorial Position Factor:

If a healthcare professional has been an editor or associate editor of a PubMed-indexed journal, a number of points are allocated. Further points may be allocated for being an advisory board of a PubMed-indexed journal and for being a reviewer of a PubMed-indexed journal.

7.=Academic Appointments Factor:

If a healthcare professional has been an instructor at a medical school, a number of points may be allocated. Points may further be allocated for being a faculty at a medical school and for being a chair of Department at medical school.

8. Referral Factor:

The Referral Information Factor is a function of the number of times the healthcare professional is referred and the qualification or reputation of the other healthcare professionals who referred the healthcare professional in real life. Or certain points can be given to each referral, and a sum of the points will be the value for this Referral Factor. This information can be obtained from public domain or from the server 106.

This Referral Factor is different than the referral a healthcare professional obtained within the system 100, for example, under the Feedback data. Those referral data are calculated under the Feedback data because the referral a healthcare professional user obtained is within the social network system, e.g., other healthcare professional users referring healthcare professional to other patients to answer their questions.

9. Achievements and Awards Factor:

In this example, points will be given if the healthcare professional has obtained some recognition or awards. For example, if he appears on a selected doctor directory, a certain number of points will be allocated. If the directory is more reputational or prestigious (for example, the US News doctor ranking, the American's top doctors list), a higher score can be given.

10. Professional Society Participation Factor:

The Professional Society Participation Factor can be a function of the credibility of each society the healthcare professional has joined. The variables can be how reputable the professional society is viewed among peers, the size of such professional society, and the number of the professional societies the healthcare professional has joined. Also a fixed value can be assigned to each organization the healthcare professional participates in. For example, if the healthcare professional is a member of a doctor society, a number of points will be assigned. For each of additional member status, further points will be given 11. Hospital Affiliation Based on the public information or the healthcare professional's input, if a healthcare professional affiliates with a best/top hospital (e.g., rank within top 17), a number of points will be allocated. If a healthcare professional is affiliated with a great hospital (e.g., rank 1-100), points may be assigned. For rest listed hospitals on certain ranking a healthcare professional affiliated, a less number of points may be assigned. For an unlisted hospital or no affiliation to any hospital, 0 points is given. The above mentioned ranking system can be any public accessible and reputable ranking system, as long as such use is consistent.

III. Calculation of Raw Feedback Data Value

The Raw Feedback Data Value indicates the quality, quantity, and recency of the healthcare professional's engagement in the system 100. Raw Feedback Data Value increases incrementally with each new unit of engagement that indicates quality. For example, if the healthcare professional provides an answer to a question provided by a patient and the patient shows appreciation (e.g., by sending appreciation message, or by recommending the answer to other people), points will be allocated to the healthcare professional. Further, if this answer is recognized by other peer healthcare professionals, more points will be allocated to the answer provider healthcare professional.

In this example, not all activities the healthcare professional users engage in are accountable. Only activities related to the quality of the engagement are counted toward Raw Feedback Data Value. For example, when the patient users followed a healthcare professional, recommended a healthcare professional, added a healthcare professional as his physician or healthcare provider, requested an appointment with the healthcare professional, voted for the healthcare professional for knowing a specific topic, thanked the healthcare professional for an answer, or shared the answer with friends either by Email, or on third party social network (e.g., Facebook or Twitter), certain points will be allocated to the answer providing healthcare professional.

Further, the recognition obtained from other peer healthcare professionals will be given higher value. For example, if other healthcare professionals send a message to a healthcare professional, other healthcare professionals referred the healthcare professional's answer to other users or refer a question to the healthcare professional, other healthcare professionals added the healthcare professional to their own network within the system 100, other healthcare professionals agreed with the healthcare professional's answer, or other healthcare professionals recommended the healthcare professional on the system 100, higher value points will be allocated to the healthcare professional.

Updating a healthcare professional's profile may cause an increase of points in the raw Feedback Data Value. This is mainly a measure to encourage a healthcare professional to update his file and improve the communication between the healthcare professionals and the patients.

The following table provides a list of accountable activities or events, each of which are associated with items to count for counting occurrences of such activities or events and are further associated with some amount of points to be allocated for each occurrence:

TABLE 1

Accountable actions and events toward the raw Feedback Data Points, each associated with some amount of allocated points.

| Action or Event | Items to count |
|---|---|
| Being shared on by Email and on other third party social network | #shares by users of this doc's content |
| Being thanked on a general question | # thanks received from users for answers |
| Being followed by a patient | #followers (users) |
| Users recommend a doc to other users | # recommendations for this doc, from users, sent to other users |
| Being added to a user's network | # users who added doc to their network |
| Being thanked with a note | #thankyou notes received |
| Other doctors send a message to this doctor, | # messages received by doc from other experts |
| Being thanked on a private message | #thanks received for private message responses |
| Vote received for knowing a specific topic (users) | # votes for knowing a specific topic received from users |
| Other doctors refer a question for answering to this doctor | # questions received by this doctor as referrals from experts |
| Being added as a patient's doctor | #users listing this doctor as their physician |
| Being requested for an doctor appointment through network | #doctor appointment requests received |
| Vote received for knowing a specific topic (experts) | # votes for knowing a specific topic received from experts |
| Doc completes the profile (minimum set required) | Key profile fields completed (About description, specialty selected, contact information filled out, special areas of expertise/interest) |
| Doctor completes the profile and adds a photo | Uploaded photo present on profile |
| Being agreed with | # Agrees received for items of content(tips, answers, guides) authored by the doctor |
| Being added to another doctor's network | # other doctors who added this doctor to their networks |
| Being recommended by another doctor on the social network | # recommendations for this doctor, from other doctors |

As shown in Table 1, even though many activities can count toward raw Feedback Data Points, activities like simply commenting on an answer without agreeing with the answer may not accumulate points for the healthcare professional.

However, the Raw Feedback Data Value will decrease with inactivity. In comparison, the Profile Data Value is mostly stable (changes only happen when the healthcare professional has a new publication, or win a new award, etc., which will not happen on daily basis). Therefore, Raw Feedback Data Value will cause the frequent changes of the Reputation Score value. Such decrease associated to inactivity under Feedback data value can be designed to be a continuous decay of total points that must be kept up with or the Raw Feedback Data Value will fall (slowly).

If the healthcare professional cannot keep up with the minimum participation score per day, the healthcare professional user account will be treated inactive. In this situation, the Time Factor will start playing roles to affect the Feedback Data Value. More specifically, the Feedback Data Value can be computed by the following formula:

Feedback Data Value=Raw Feedback Data Points*TimeFactor.

Time Factor:

Time Factor reflects the activeness of a healthcare professional user of the system 100. When a healthcare professional becomes inactive on the system 100, a rapid, reversible decay in the score occurs. This decay will be reversed when the healthcare professional re-engages and generates more points through activity on the system 100. The time decay for inactivity may produce a significant drop over some initial period of inactivity (e.g., inactivity over the first 30 days may result in losing 50% of the Feedback Data value), then loses another value (e.g., 40%) over another period (e.g., the next 11 months), reaching and remaining at 0.1 after one year of inactivity.

In addition, a multiplier may be associated with the status of a healthcare professional, and can be assigned to the healthcare professional and contribute to the raw Feedback Data calculation. For example, if a healthcare professional is listed in a selected directory (e.g., a doctor directory, etc.), he can be assigned to have a 1.4 multiplier and the accumulation of the raw Feedback Data Points will be faster. In this situation, the healthcare professional's Feedback Data Value could be calculated as follows:

Feedback Data Value=Raw Feedback Data Points*Time Factor*Status Multiplier

As described above, when the healthcare professional becomes inactive, a rapid, reversible decay in the Feedback Data Value occurs. However, this decay is reversed when the healthcare professional re-engaged and generates more points through activity on the system 100. The healthcare professional can restore the Feedback or Endorsement Score by re-engagement. Upon re-engagement, the Raw Feedback or Endorsement Score returns to the previous value diminished only by the decay of points equal to some unrecoverable amount of decay representing a required minimum participation per day times number of days since last activity, for example:

Recovered Raw Feedback Data Value=Raw Feedback Data Value before the decay(the inactivity)−minimum participation required/day*number of days since last activity While the Reputation Score is discussed herein primarily with respect to a numerical value, the Reputation Score may alternatively be represented by a symbol, such as stars. In an embodiment, the Reputation Score ranges from 0 to 5 stars, reflecting the peer-recognition that the healthcare professional has received within the system 100, as well as relevant public and other information, as described above, which may include: agrees, votes and recommendations from other healthcare professionals; years of experience; quality of healthcare professions who refer them; education information; board certifications; other professional accomplishments; and thanks, votes and recommendations from patient users. The number of stars (or other symbol) to be given to a particular healthcare professional may be based on a numerical result (e.g., as discussed above), with ranges of numerical values being associated with the number of stars to be given (e.g., 0-20=0 stars; 21-40=2 stars; 41-60=3 stars; 61-80=4 stars; 81-100=5 stars).

Referrals or Votes Provided to Healthcare Professionals

In further embodiments, the present disclosure provides systems and methods to allow expert users (e.g., "professionals" or the like) to identify areas of interest and expertise for purposes of identifying themselves to third parties as having knowledge and interest in these topics, and for interacting with a system that provides them with an opportunity to display their expertise and express their interest through creating content (including in the form of answering questions) on these topics.

Figure 3:
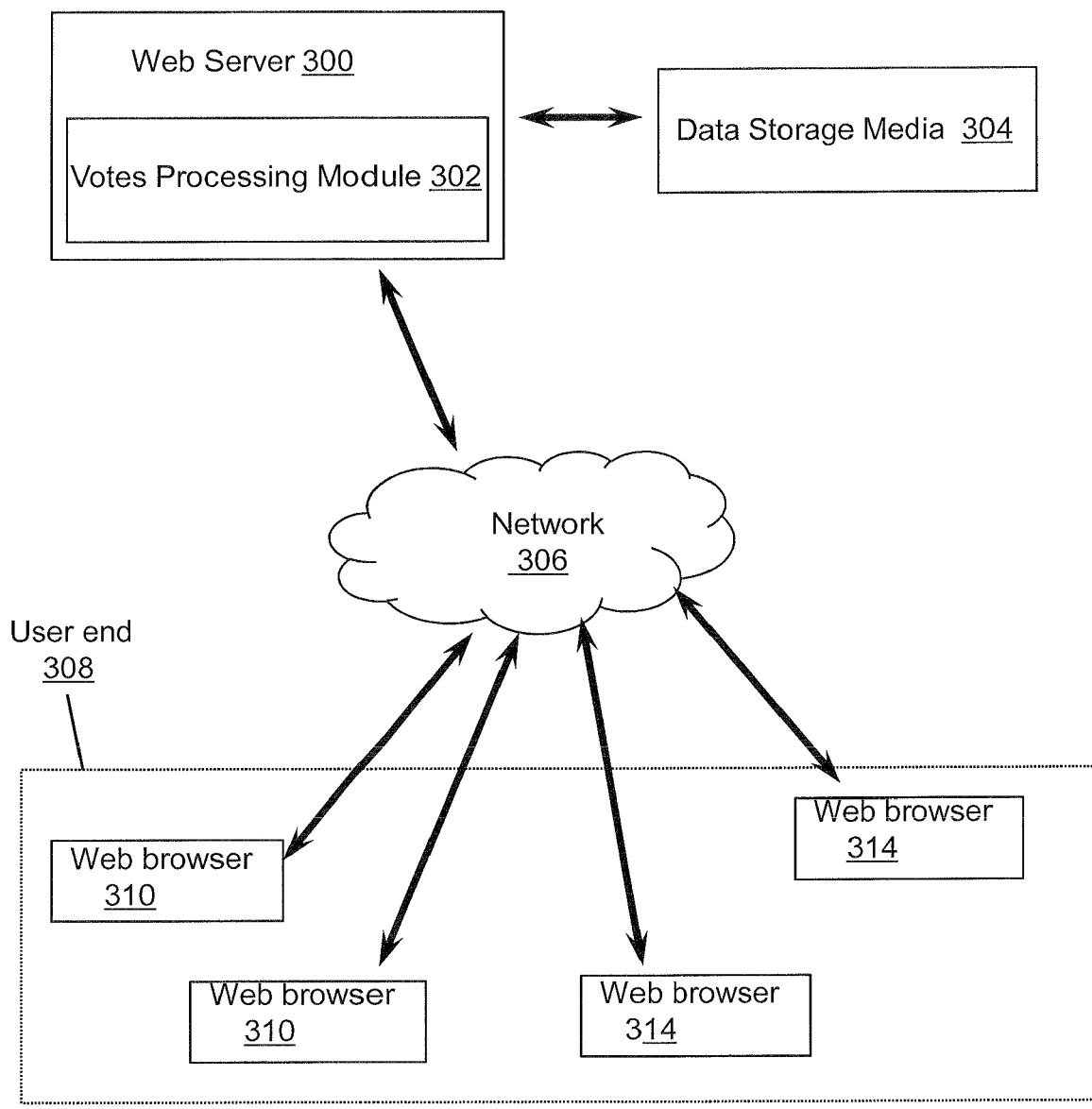
FIG. 3 is a diagram illustrating components of an example of a system in accordance with one or more embodiments of the present disclosure.

FIG. 3 is a schematic illustration of a healthcare professional evaluation system 30 (which may be referred to hereinafter as 'system 30'), in accordance with embodiments provided by the present disclosure. The system 30 includes one or more user computer devices 310 (described herein as "patient computer devices"), one or more healthcare professional user computer devices 314 (described herein as "doctor computer devices"), a web server 300 and data storage media 304. A user end 308 (e.g., web browser displayable on a computer device) provides user interface, through which the users can cast votes or search and access content they are interested in, as well as search doctors. The web server 300 is electronically accessible through at least one network system 306 to multiple computer devices (e.g., patient user computer devices 310, healthcare professional user devices 314). The network system 306 may include any type of network infrastructure, such as the Internet, or any other wired, wireless and/or partially wired network.

The server 300 may be or include any database capable of storing and/or providing access to information, such as an electronic database, a computer and/or computerized server, database server or generally any network host capable of storing data and connected to any type of data network. Further, the server 300 may include or be a part of a distributed network or cloud computing environment. Any type of electronic and/or computerized device that is capable of storing information may be included as the server 300, and is considered within the scope of this disclosure. The server 300 may include computer-readable storage media, and a processor for processing data and executing algorithms, including any of the processes and algorithms set forth in this disclosure.

Web server 300 hosts, fully or partially, or otherwise accesses multiple application logic components (e.g., a Votes Processing Module 302). As is understood by persons skilled in the relevant art, modules shown in FIG. 3 may represent sets of executable software instructions as well as the corresponding hardware (e.g., memory and processor) for executing the instructions. The server 300, votes processing module 302, and network system 306 may include a variety of hardware and software components to provide successful functioning of the server 300 and the module 302, as is well-known within the art. Further, any features, characteristics, designs and/or functions that are known within the art may be included with the system 10 to further enhance its efficiency.

The system 30 may further include one or more patient computer devices 310 and one or more doctor computer devices 314. The patient computer devices 310 and doctor computer devices 314 may be any computerized devices capable of communicating with the server 300, for example via a network system 306. The one or more patient computer devices 310 may be operated by a patient user (which may be any user who votes using the system 30 or otherwise seeks information related to professional users of the system 30, and need not be an active patient of any treating physician or medical caregiver) of the system 30, and the one or more doctor computer devices 314 may be operated by any doctor user of the system 30 (which may be any user who may be evaluated using the system 30, and may include any healthcare professional, such as a primary care physician, medical doctor, nurse, medical staff or other medical professional, or any representative thereof).

The data storage media 304 is a computer-readable storage medium, which may be any device or medium that can store code and/or data embodying or used by any one or more of the methods or functions described herein. This includes, but not limited to, volatile memory, non-volatile memory including by way of example semiconductor memory devices, e.g., Erasable Programmable Read-Only Memory (EPROM), Electrical Erasable Programmable Read-Only Memory (EEPROM), and flash memory devices, magnetic storage such as internal hard disks and removable disks and optical storage devices such as disk drives, magnetic tape, CDs (compact discs), DVDs (digital versatile discs or digital video discs), or other media capable of storing computer-readable media now known or later developed. The data storage media 304 may be included in, or electronically accessible by, the web server 300.

While the computer-readable medium is shown in some embodiments to be a single medium, the term "computer-readable medium" may include a single medium or multiple media (e.g., a centralized or distributed database, and/or associated caches and servers) that store the one or more instructions or data structures. The term "computer-readable medium" shall also be taken to include any tangible medium that is capable of storing, encoding or carrying instructions for execution by the computer and that cause the computer to perform any one or more of the methodologies of the present invention, or that is capable of storing, encoding or carrying data structures used by or associated with such instructions.

Set Topics or Practicing Areas for Users to Cast Vote on

Figure 4:
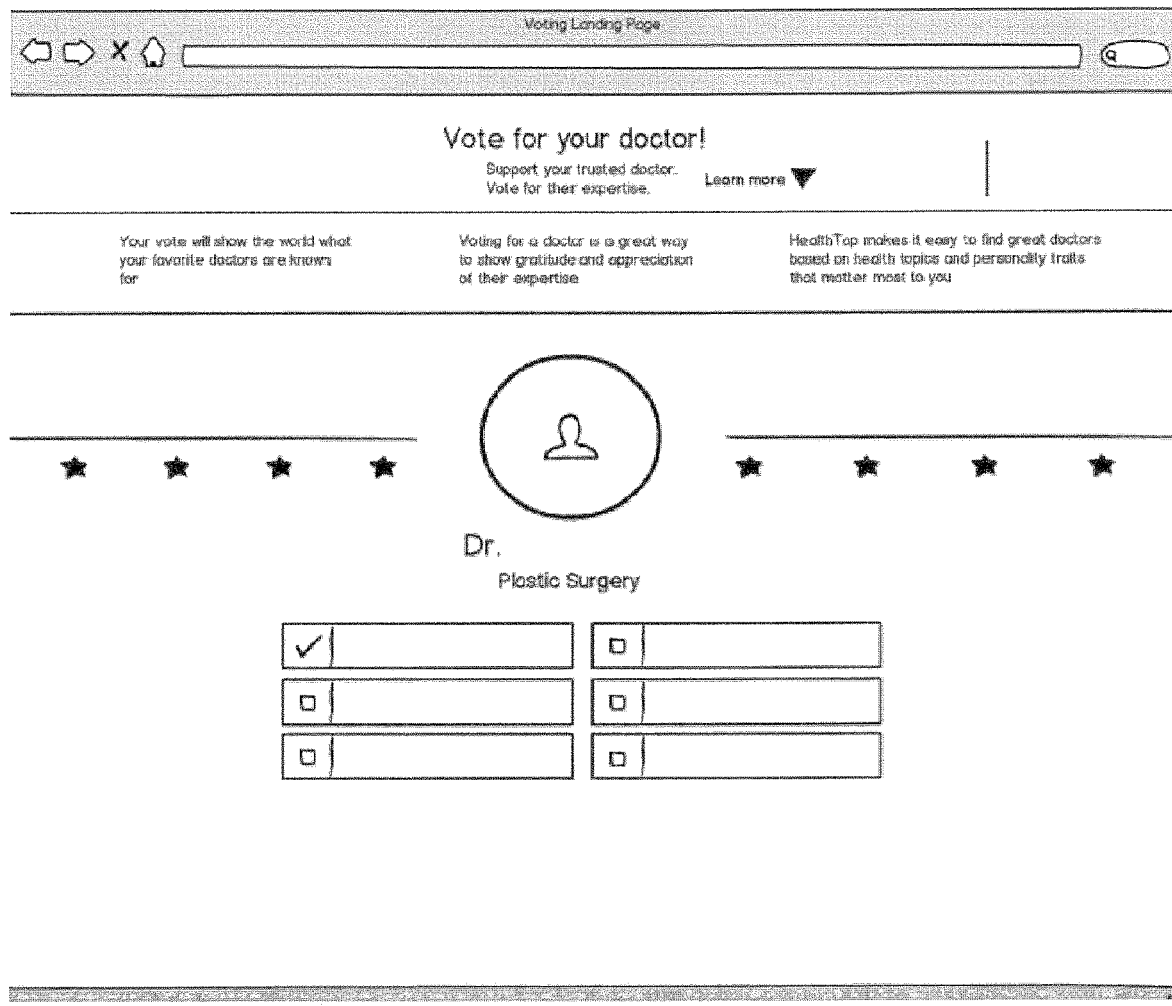
FIG. 4 illustrates a Voting Page presented to the users to vote for a doctor, in accordance with embodiments provided by the disclosure.

The topics or practicing areas for voting on can be identified by the doctor himself. The doctor can either identify his practicing area or an area of interest where he has done some research or had a publication in the related area. If the doctor did not identify the above area during the registration process, the system 30 can also establish such list of topic or practicing area based on the doctor's specialty and peer reviewed publications. In one embodiment, the users (e.g., patient users) also have an option to add a new area to vote for the doctor. Such options can be shown in the last box and the voters may fill in new content identifying a new topic or practicing area (as shown in FIG. 4).

However, when the system 30 generates such list for the users to vote, there may be some practices or topics which are related, but described in a different term. The system 30 has a processing module 302 to organize such different inputs, merge related topics and provide topics which are distinctive from each other.

Differentiate the Votes from Doctors and Votes from Patients

It is important to differentiate the votes from licensed medical professionals and regular patient users, as each type of user may have more informed or otherwise relevant input. For example, patient votes may be particularly relevant with respect to a doctor's bedside manner evaluation. However, when it comes to evaluating the practicing skills of a doctor, patients might lack professional knowledge to provide more objective evaluations.

To that end, an authentication module may be included within the system 30 to verify the users who identify themselves as healthcare professionals. The authentication module may be included in or otherwise accessible to the Votes Process Module 302 and may include or access a database (e.g., stored in data storage media 304) having a directory of medical professionals in U.S. and other data related to professional performance of each licensed medical professional. When medical professionals register or sign in the system, the authentication module generally requires the user to verify the existing information in the system and provide more information related to his professional performance. However, to guarantee the accuracy and currency of the medical professionals' qualification, all medical professionals are screened for credentials based on the public information released by impartial third party or public registered information, for example, each state's licensing board. Such information may be stored in the system 30 (e.g., in data storage media 304), and may be frequently updated in responding to the newly released public information. When a medical professional is verified by the system 30 to be currently qualified to practice, the system 30 will allow the medical professional to cast votes or agree on other medical professionals' answers.

Voting User Interface

FIG. 4 illustrates one example embodiment of the Voting Screen the users may interact with. This page can be accessible through a graphitic user interface element. In the center of this page, the medical professional's name and specialty is clearly identified. Under the doctor's name, there are multiple boxes listing the topics or practicing areas that the users can cast votes on. These voting topics or practicing areas are decided by either the doctors themselves or by the system 30 based on the doctor's publication and other related information (e.g., specialty board certificate).

However, a vote from patient users is calculated separately from a vote casted by credentialed doctors. The votes from patient voters are categorized as bedside manner votes under each topic or practicing area (shown in FIG. 5, Section 1). The votes from patients do not provide resources of where these votes are collected from. However, for the votes from credentialed doctors, the system 30 not only provides the number of total votes, but also provides an access for the users (both doctors and patients) to find out which doctors casted votes for the present doctor (e.g., the doctor being displayed to the user). This not only provides transparency of the voting process, but also improves the credibility of the voting results. For example, if a doctor is voted by many doctors in the same field or practicing area, the patient will find such voting demonstrated the reputation of the doctor in the pertinent field. Also when the voting source is transparent, the comments will tend to be more objective.

The basis for the voting can be either from the real life experience, for example, doctor visit, or from reading the content generated by the doctor, for example, the answers provided by the doctor and solicited by the patients on a social network. In either situation, such rating is based on actual knowledge of the doctor's practicing skills and knowledge.

Presentation of Votes

Figure 5:
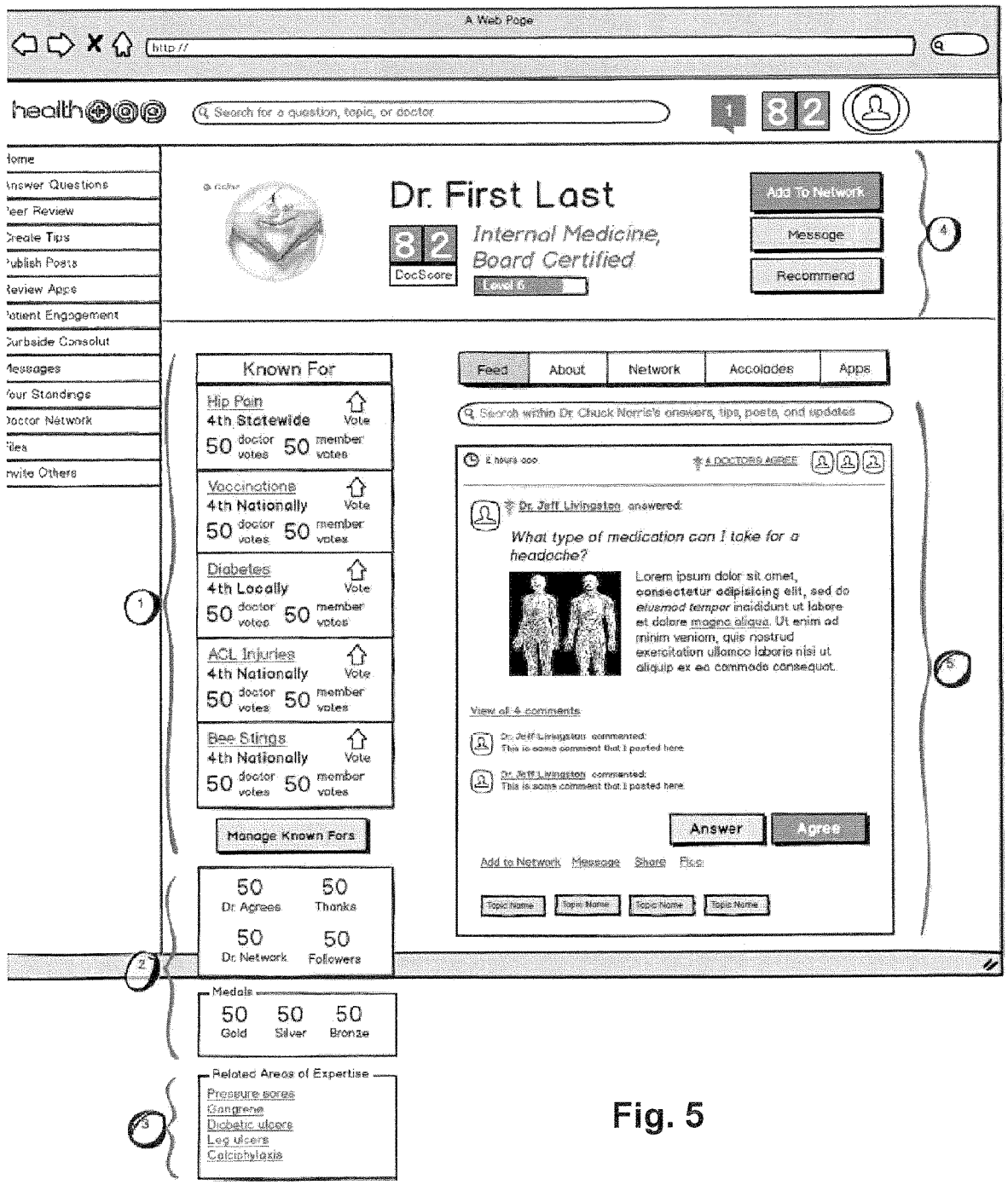
FIG. 5 illustrates one example of a Voting Result Delivering Page where certain related content can also be delivered along with the Voting Result, in accordance with embodiments provided by the disclosure.

The votes casted by the users are processed by the Votes Processing Module 302 before being presented in the Voting Result Presentation Page. FIG. 5 illustrates an example embodiment of the Voting Result Presentation Page. Section 1 presents the topics or the practicing areas that a doctor obtained votes upon. For instance, in this example, the doctor obtained votes on topics of Hip Pain, Vaccinations, Diabetes, ACL Injuries and Bee Stings. As stated before, the votes from doctors and from the patients are calculated separately. For example, under the topic Hip Pain, the present doctor received 50 doctor votes and 50 member votes (votes from non-healthcare professional users). Such divided source of votes helps users appreciate the recognition the doctor received among peers, at the same time also acknowledge the communication skills the doctor has with patients.

Second, the identities of all of the 50 doctors casting votes for the present doctor are transparent to the users. For example, the user can simply click the 50 doctor votes and learn who voted for the present doctor under the Hip Pain topic.

Third, the votes are calculated locally, statewide and nationally (e.g., nationwide, state wide, or locally). If the doctor obtains top number of votes locally (for example, within top 10 in a local area), such information will be provided in that specific category of specialty of practicing area (e.g., FIG. 5, Section 1, below "Diabetes"). If the doctor has top number of voting nationally (for example, with in top 20 national wide), such information will also be presented under that category (e.g., FIG. 5, Section 1, below "Vaccinations"). This is helpful for the patients who are looking for a local doctor that he can make a doctor visit and do follow up examination. A national top voting of a doctor may help a patient make decisions in seek specific medical service when he/she have a very complicated disease or health issue.

Section 3 shows related areas of expertise and other topics that a doctor is known for, but did not receive votes in these practicing areas yet. Section 4 shows the basic information about a doctor including First and Last name, specialty, Board Certification, DocScore (can be a external doctor evaluation system showing the doctor's professional reputation or skills), Photo, and graphical user interface elements for connecting with this doctor.

Last, such voting result can be presented together with other content provided by the doctor, for example, the answers, tips or posts the doctor provided before, the license information or publication list the doctor has, or network information the doctor has connection with (Section 5). Further, the voting results may be presented together with other statistics of the present doctor, for example, the statistics of how many "doctor agrees" the doctor received when he provided answers to the questions posted by the users, how many thanks the doctor received from the patient users when he provided such answers, or the number of doctor and patient followers they have (Section 2). Also how responsive the doctor is may also be presented (responsiveness). Such evaluation can be based on the percentage of the questions the doctor answered out of the number of questions being given by the system.

The system 30 can also provide a measure to evaluate the quality of the content the doctor rendered. For example they system will give the doctor medals when certain content received many "thanks" from the patients, e.g., a brown medal for over 5 thanks, a silver medal for over 10 "thanks," and a gold medal for over 15 "thanks" (the bottom section of Section 2).

Such collected information based on different source provides a user a comprehensive understanding of the present doctor's performance and practicing skills, where the patients have more source to learn about the present doctor and decide whether he will follow up with the doctor further, for example, ask one to one question or make a doctor visit appointment.

In addition, such voting result can be presented also with other ranking or rating results based on different approach or basis. For example, there could be another separate system evaluate the doctor solely based on the merits of the doctor (e.g., where he obtains education, what publications he have), and presented together with the votes. Therefore, the users have an understanding of how the doctor is evaluated by the patients, as well as by the peer doctors.

Providing Answers to User-Submitted Questions

In further embodiments, the present disclosure provides systems and methods for providing trustworthy answers to health questions (or questions in any other field of knowledge) in an efficient and timely manner. Various aspects of the inventive methods and systems provided herein aims at increasing the reliability of the answers to health (or other) questions and reducing the response time. The present invention enables any patient (or other users) to solicit answers for health (or other) questions in a social network setting. Moreover, users may search and view existing questions (as well as related answers) related to desired topics or areas of practice.

In accordance with embodiments provided herein, the answers are delivered solely by professionals having verified qualifications (e.g., licensed doctors) and in good standing within their respective profession. These answers are also curated by other qualified professionals (e.g., doctors). Other professionals (e.g., doctors) can show they agree with the answers and thus affect the credibility of the answer. The more "agrees" an answer obtains, the more prioritized (i.e., higher ranking) the answer is presented to users in a list of answers. In addition, the answer will be provided promptly. In one embodiment, the answer will be supplied within 24 hours.

Figure 6:
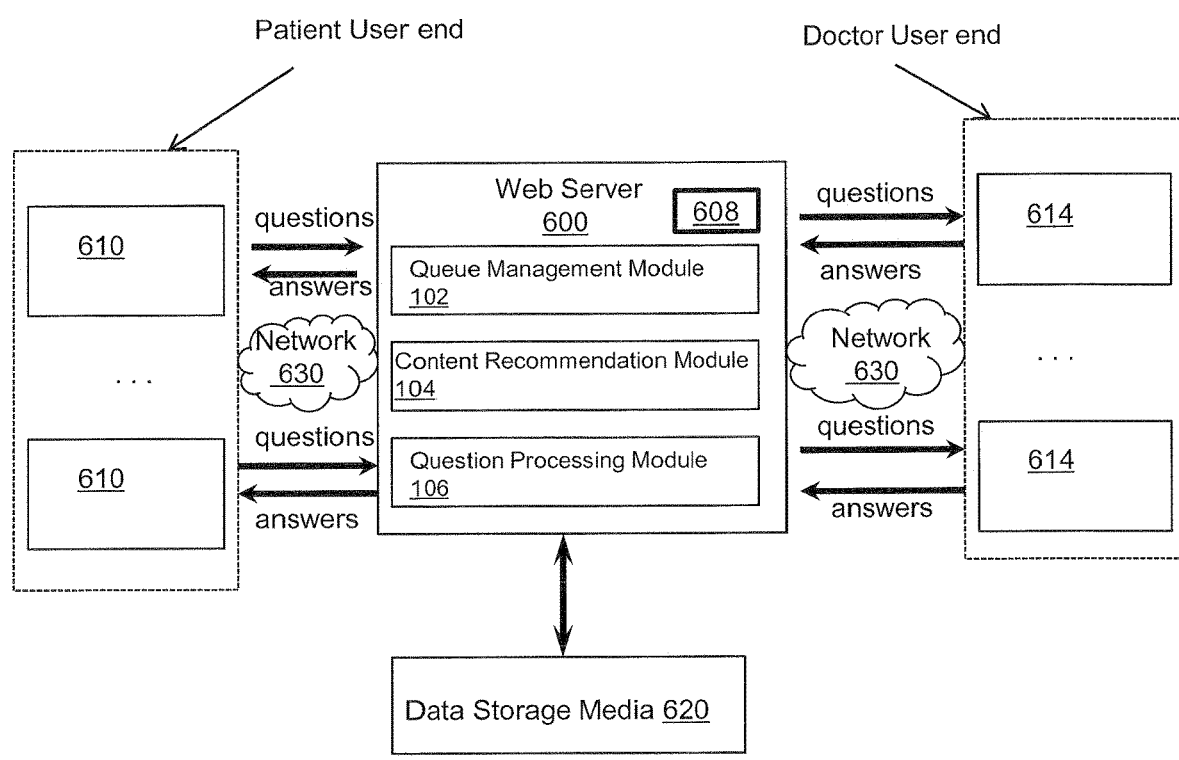
FIG. 6 is a schematic illustration of a system for providing answers to user-submitted questions, in accordance with embodiments of the present disclosure.

FIG. 6 is a schematic illustration of a system for providing answers to user-submitted questions 60 (which may be referred to hereinafter as 'system 60'), in accordance with embodiments provided by the present disclosure. The system 60 includes one or more user computer devices 610 (described herein as "patient computer devices"), one or more professional user computer devices 614 (described herein as "doctor computer devices"), a web server 600 and data storage media 620. The web server 600 is electronically accessible via at least one network system 630 to multiple user ends (e.g., patient user end having one or more patient computer devices 610; doctor user end having one or more doctor computer devices 614). The network system 630 may include any type of network infrastructure, such as the Internet, or any other wired, wireless and/or partially wired network.

The server 600 may be or include any database capable of storing and/or providing access to information, such as an electronic database, a computer and/or computerized server, database server or generally any network host capable of storing data and connected to any type of data network. Further, the server 600 may include or be a part of a distributed network or cloud computing environment. Any type of electronic and/or computerized device that is capable of storing information may be included as the server 600, and is considered within the scope of this disclosure. The server 600 may include computer-readable storage media, and a processor for processing data and executing algorithms, including any of the processes and algorithms set forth in this disclosure.

Web server 600 hosts, fully or partially, or otherwise accesses multiple application logic components (e.g., a Queue Management Module 602, Question Processing Module 604, Content Recommendation Module 606 and Authentication Module 608). As is understood by persons skilled in the relevant art, modules shown in FIG. 6 may represent sets of executable software instructions as well as the corresponding hardware (e.g., memory and processor) for executing the instructions. The server 600, modules 602, 604, 606, 608, and network system 630 may include a variety of hardware and software components to provide successful functioning of the server 600 and the modules 602, 604, 606, 608, as is well-known within the art. Further, any features, characteristics, designs and/or functions that are known within the art may be included with the system 60 to further enhance its efficiency.

The system 60 may further include one or more patient computer devices 610 and one or more doctor computer devices 614. The patient computer devices 610 and doctor computer devices 614 may be any computerized devices capable of communicating with the server 600, for example via a network system 630. The one or more patient computer devices 610 may be operated by a patient user (which may be any user seeking health-related information, and need not be an active patient of any treating physician or medical caregiver) of the system 60, and the one or more doctor computer devices 614 may be operated by any doctor user of the system 60 (which may be any user to whom access to provide answers to pending questions has been granted, and may include any healthcare professional, such as a primary care physician, medical doctor, nurse, medical staff or other medical professional, or any representative thereof).

The data storage media 620 is a computer-readable storage medium, which may be any device or medium that can store code and/or data embodying or used by any one or more of the methods or functions described herein. This includes, but not limited to, volatile memory, non-volatile memory including by way of example semiconductor memory devices, e.g., Erasable Programmable Read-Only Memory (EPROM), Electrically Erasable Programmable Read-Only Memory (EEPROM), and flash memory devices, magnetic storage such as internal hard disks and removable disks and optical storage devices such as disk drives, magnetic tape, CDs (compact discs), DVDs (digital versatile discs or digital video discs), or other media capable of storing computer-readable media now known or later developed. The data storage media 620 may be included in, or electronically accessible by, the web server 600.

While the computer-readable medium is shown in some embodiments to be a single medium, the term "computer-readable medium" may include a single medium or multiple media (e.g., a centralized or distributed database, and/or associated caches and servers) that store the one or more instructions or data structures. The term "computer-readable medium" shall also be taken to include any tangible medium that is capable of storing, encoding or carrying instructions for execution by the computer and that cause the computer to perform any one or more of the methodologies of the present invention, or that is capable of storing, encoding or carrying data structures used by or associated with such instructions.

Authentication of the Doctors' Credentials

In the system 60, answers are provided exclusively by licensed doctors with good standing. The good standing status requires that no sanctions or disciplinary restrictions are in effect against the doctor. Neither can the doctor be a defending party in any open malpractice suit. The term "doctor" is used herein in a broader meaning to refer to any medical practitioner or healthcare professional providing healthcare services of any kind, or any kind of services appurtenant to healthcare. Further, while the present disclosure is described for exemplary purposes with respect to doctors and patients, the present invention is not limited for use in any particular profession or area of expertise. Rather, the systems and methods provided herein are applicable to users (i.e., those submitting questions) and professionals or persons having particular expertise (i.e., those providing answers) in any given field.

Users without a license to practice medicine or doctor users without good standing status do not have access to answer the questions presented by users of the system 60. Thus, it is important to verify the identities of those users who claim they are doctors with good standing. To this end, the system 60 includes an authentication module 608 to verify the users who identify themselves as doctors licensed to practice medicine in certain jurisdiction and in good standing in that jurisdiction.

The authentication module 608 includes or has access to a database (e.g., stored in data storage media 120) including directories of doctors and other data related to professional performance of each licensed doctors. When a doctor registers or signs in the system 60, the authentication module 608 may require the doctor user to verify the existing information in the system 60 and provide further information related to his professional performance. However, to guarantee the accuracy and currency of the doctors' qualification, all doctors are screened by the authentication module 608 for credentials based on information released by impartial third parties or public registered information, for example, each state's licensing board (shown in FIG. 7, Step 216). Such information is stored in the system 60, and is frequently updated to include newly released public information.

If the doctor passes the screening and is validated by the authentication module 608 to answer questions, the authentication module 608 will grant the doctor access through the system 60 to provide answers to pending questions. Such grant of access to the questions is revocable and conditioned on the current good standing status of the doctor. If the doctor's good standing status changes and does not satisfy the requirement anymore, the system will block the doctor's access to pending questions and such blocking will remain in place until the good standing status is resumed.

In addition, some or all of the doctor's information related to merits, practicing skills, and professional performance may be transparent to all the users (i.e., patient users and doctor users). The doctor's identity (e.g., name, photo, location, specialty and/or any other identifying information) will be presented next to the answer he provided. Through clicking the doctor's profile photo, the users can access the doctor's profile and learn more about the doctor's skills and credentials. The complete transparency fosters the trust between doctors and patients using the system 60 and encourages the interaction among the doctors and the patients. Further, when a doctor agrees with an answer already provided by another doctor user in the system 60, his identity will also be shown next to the answer. The users can similarly learn more about the doctors who agreed with the answer and what are their professional credentials.

Registered users (e.g., patient and doctor users) of the system 60 have profiles, which are well-known in social networks and related fields. The profiles may be a profile containing pages and/or information visible to the public generally, information that is visible only to the user herself, information visible only to particular users specified by the user, information visible as specified by the user, and information that may not be visible to other users. The doctors' profiles are generally visible to all of the users of the system 60. All users can view the doctors' profiles and can find out the doctors' credentials.

Question Processing Module

When a user inputs a question or key words (e.g., using an input box provided by the system 60 and displayed in a graphical user interface of the user's computer device 610) to solicit answers, the string content in the input box will be processed by the Question Processing Module 606 (FIG. 7, Step 202) and key words will be extracted. Techniques for identifying and extracting key words are known within the relevant field, and any such techniques may be utilized for key word extraction by the Question Processing Module 606. The key words are then associated by the Question Processing Module 606 with single or multiple predefined topic tags which may be stored, for example, in a database in data storage media 620. Such topic tags may include collections of disease names, treatment methods, diagnosis, surgical procedures, hot topics, areas of practice and the like. The topic tags can be associated with closely related terms either by meaning or formality, such that the topic tags applied to variable forms of terms referring to the same topic. For example, the topic tags may be associated with misspellings, singular and plural forms and different expression of the same term. Thus, closely related terms regarding a specific topic can be organized together by topic tags. The system 60 has stored a great accumulation of these topic tags and these topic tags are further organized by Group ID.

The Group IDs are the next higher level of organized subjects than the topic tags and may be stored in a database in data storage media 620 and associated with relevant topic tags. In one embodiment, the Group IDs may be disease names, with each Group ID being associated with a collection of topic tags related to symptoms, conditions, side effects, treatment, procedures and medications for the disease. Such a higher level organization of information is important for functions providing related content in various situations, as the related content can be extracted from the pool of content sharing the same group IDs.

The association relationships between a question, topic tags and Group ID are stored (e.g., in data storage media 620) together with the question and their answers. The questions are organized by the topic tags and the Group ID and will be extracted by the Question Processing Module 606 from the database based on the patient user's request (e.g., presenting similar questions before the user proceed to post the question). For example, when a user wants to search some specific content, he can just input a key word and the Question Processing Module 606 will recognize that key word and match it up with the existing tags and extract related questions and answers from the database and display the related content. If there are no close existing tags, the system 60 can provide content sharing the same Group IDs with the requested content.

Providing Answers in a Timely Manner

It is important that the answers to health questions be provided in a timely and efficient manner. Questions related to health care often need to be answered quickly. Some actions might need to be taken promptly regarding certain health concerns. The patient often would significantly benefit from a quick answer, and an untimely answer may be of little or no use. A quick answer also helps reduce the anxiety caused by some suspicious symptoms. The system 60 prevents, or significantly reduces the likelihood of, questions from sitting in the system 60 for long periods of time without being answered. In an embodiment, all the questions will be answered within 24 hours from being posed by users in the system 60. To assure the questions are answered promptly, the system 60:

a. Reduces traffic by presenting similar questions and answers to the user before the user proceeds to post a new question;

b. Organizes questions in a reverse chronological order where the oldest question in the system is placed on the top of the question list presented to the doctors;

c. Sends questions to doctors who are specialists in areas relevant to the questions, and improve the efficiency of the system;

d. Provides similar unanswered questions to the doctor after the doctor provides an answer to a question;

e. Gives the doctors awards or credits for answering additional questions or questions that are needed to be answered urgently.

f. Messages the patient user to give him/her the choice to modify the question if the question has not been answered for a long time.

1. Reduce Traffic by Presenting Similar Questions to the User Before the User Posts a New Question.

The system 60 can guarantee questions being answered within a short period of time, e.g., 24 hours. One way the system 60 can efficiently and promptly provide answers promptly is by avoiding processing (i.e., sending to doctors) questions that have already been answered in the system 60. In one embodiment, the users (mainly patient users) will be presented with a list of questions which are identified by the system 60 (e.g., by the Question Processing Module 606) that are either similar or related to the question the user just posted.

The related questions may have been previously answered and stored in the system 60 (e.g., in Data Storage Media 620) together with associated topic tags and Group IDs, assigned by the Question Processing Module 606. Their related answers are tagged and categorized separately as well. The previously answered questions that are displayed to the user are selected based on relevancy. The relevancy is determined by the system 60 (e.g., by the Question Processing Module 606) through analyzing the topic tags associated with existing questions stored in the system 60 and those associated with the present question. The more topic tags a previously answered question and the present question have in common, the higher the degree of relevancy the system 60 will determine to exist between the previous question and the present question.

In addition, each answer may be assigned an Answer Score. Answer Score reflects the confidence in the content of the answer. The Answer Score may be based on a variety of factors, including: a. the reputation of the author; b. "agrees" the answer obtained from other doctor users; c. "thanks" the answer received from patient users; d. number of times that the answer has been shared with other users; e. the length of the answer (the longer answer has more details and will be given higher score). Such an Answer Score can be a function of any combination of the above factors. The factors can be given different weights in computing the Answer Score. The Answer Score may be generated by the Question Processing Module 606, or by a separate tool contained within the system 60.

The list of related previous questions will be presented to the user (e.g., displayed on the patient computer device 610) in a ranked order based on both the relevancy of the topic tags and the value of the Answer Score. A highly related question having an associated answer with a high Answer Score will be ranked highly, and thus shown on top of a Related Questions Presentation Page. However, the user makes the final decision as to whether the proposed question is already sufficiently answered or not. In one embodiment, after being presented with existing related questions and/or their associated answers on the Related Questions Presentation Page, some users might decide that their questions already have been answered and stored within the system 60, and they will not proceed to post the question. In this way, some amount of traffic, data storage and redundancy will be reduced. However, if the user decides his question has not been answered, the system 60 will allow the user to proceed to post his/her new question.

In general, the user can post questions for any doctor to answer. However, to increase efficiency, in one embodiment, the system 60 sorts the questions and sends the questions to doctors who claim specialty in related area or practice. The system 60 can also allow the user to designate a specific doctor to answer the question.

2. Organize Questions in a Reverse Chronological Order Where the Oldest Question in the System is Placed on the Top of the Question List—Queue Management The Queue Management Module 602 (FIG. 6) operates to organize the to-be-answered questions in the system based 60 on the time the question is submitted. Therefore, the longer the question sits unanswered in the system 60, the higher priority will be assigned to this question to be processed (i.e., answered) by the system 60. In addition, Queue Management Module 602 also operates to select to-be-answered questions and present them to individual doctor users. With the organization by the Queue Management Module 602, the doctor users will not see a very long list of unanswered questions (e.g., a list of all pending unanswered questions). Rather, the doctor will see only those questions selected for the doctor by the Queue Management Module 602 (e.g., based on the doctor's specialty, location or other relevancy consideration) on the Question Presentation page (shown in FIG. 8).

The Queue Management Module 602 compiles the to-be-answered questions list based the following considerations: a. Time of submission: the oldest questions are given priority to be presented on the Question Presentation Page; b. The patient user's special request for a fast answer: upon a user's request to process the question faster, this question will be marked and automatically moved up to or near the top of the list; c. Relations to the specialty the doctor claimed: Queue Management Module 602 will send questions to the doctor within his specialty by default; d. The geographic location of the doctor: the Queue Management Module 602 will automatically send the questions to doctors who has closer geographic location to the patient user who posted the question; e. Whether the doctor has provided similar content or answers to similar questions before: the Queue Management Module 602 will send to the doctor questions that he has shown knowledge on.

3. Send Questions to Doctors Who are Specialized in the Area or Practice the Questions Related and Reduce the Responding Time The doctor can specify fields that he/she has expertise or feels more comfortable answering questions in. If the doctor user does not claim a specialty, the system 60 will assign a specialty tag to the doctor based on his/her licensing information and publications. The specialty tag may be associated with the doctor, for example, in the doctor's profile which may be stored in a database in or accessible to the system 60. Such specialty tag allows the Queue Management Module 602 to only send the doctor questions related to his specialty and let the doctor answer questions he feels more comfortable with. However, such specialty screening is optional and the doctor has a choice at the Question Presentation Page to view either the questions solely from his own specialty or from all fields.

4. Show the Doctors Similar Questions After the Doctor Answered Related Questions In addition, after a doctor answers one question, a list of similar unanswered questions can be presented to the doctor in a pushed message (e.g., the Queue Management Module 602 may push such questions to the doctor's user device 614). Such a list of similar questions obtained through the same sorting and organizing techniques as described with respect to presenting a Related Questions Presentation Page to the users.

5. Provide Awards or Credits to Doctors for Answering High Priority or Additional Questions.

Figure 8:
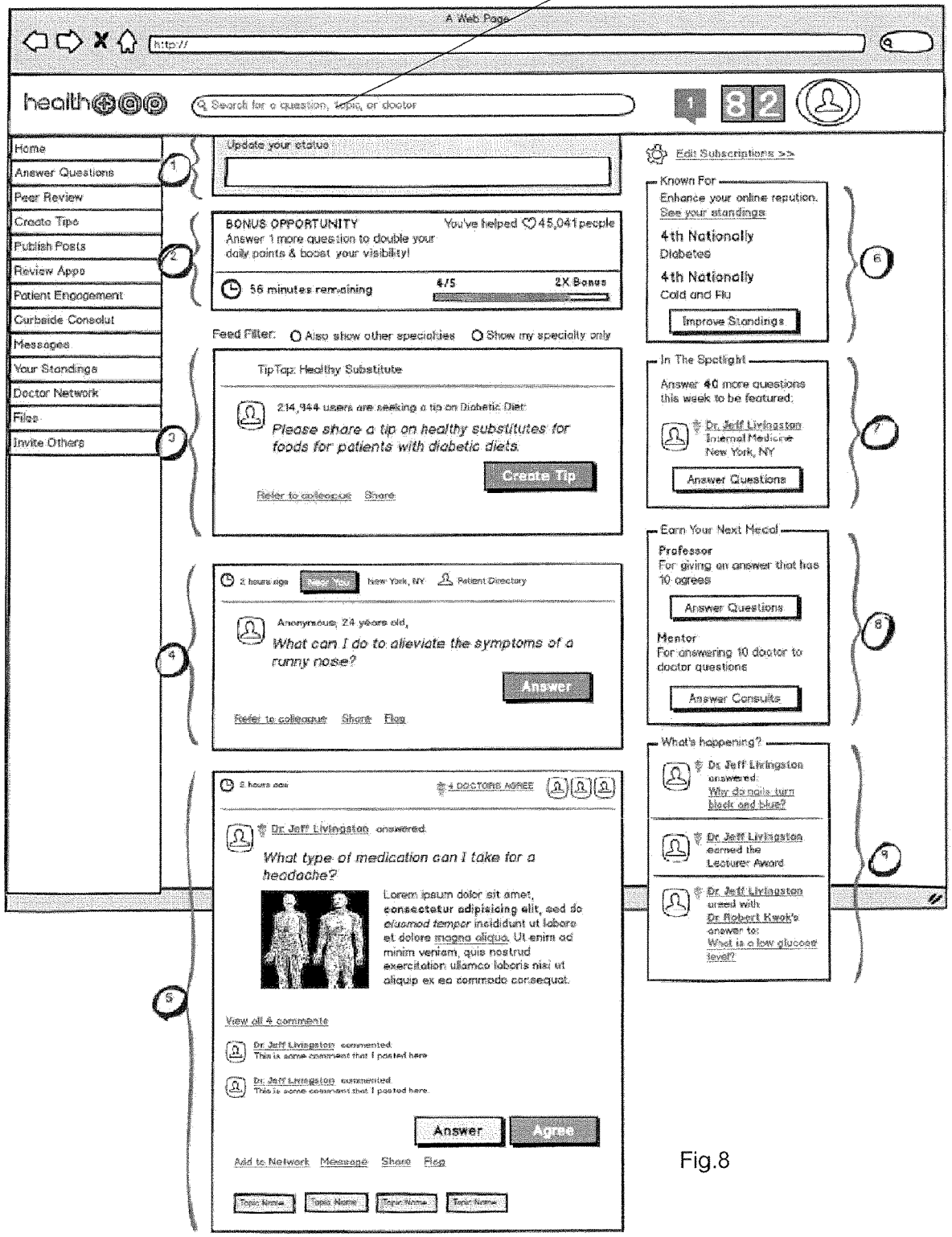
FIG. 8 illustrates a webpage or other graphical user interface (the "Question Presentation Page") presented to doctors, in accordance with embodiments of the present disclosure.

An award system may be established to encourage the doctors to answer more questions, especially when the unanswered questions in the system 60 are backlogged. As shown in FIG. 8 (section 2), the doctors are provided an opportunity to gain an award or credits (e.g., bonus double daily participation points) by answering one more questions. Further, bonus points may be allocated to doctor users for answering high priority or urgent questions in the system 60. Such bonus points may be utilized to increase a doctor's status or ranking in the system 60, or may be provided to a doctor evaluation system or recommendation system which may utilize the doctor points as a factor in evaluating, ranking or recommending doctors. The system 60 may be integrated with or otherwise communicatively coupled with such an evaluation or recommendation system, thereby providing benefit to the doctors who answer questions on the system 60 by facilitating an increased status or ranking.

6. Message the Patient User to Give Him/Her the Choice to Modify the Question if the Question has not Been Answered for a Long Time.

In one embodiment, the system 60 monitors questions in view of a time limit within which questions should be answered. Such time limit can be decided based on the traffic volume of the server. When a question is not answered within this time limit, the system 60 will send a message to the question posting user to remind him/her that his/her questions are still not answered. The system 60 can also give the user a choice to modify the questions and try again.

Answer Presentation Page

Figure 9:
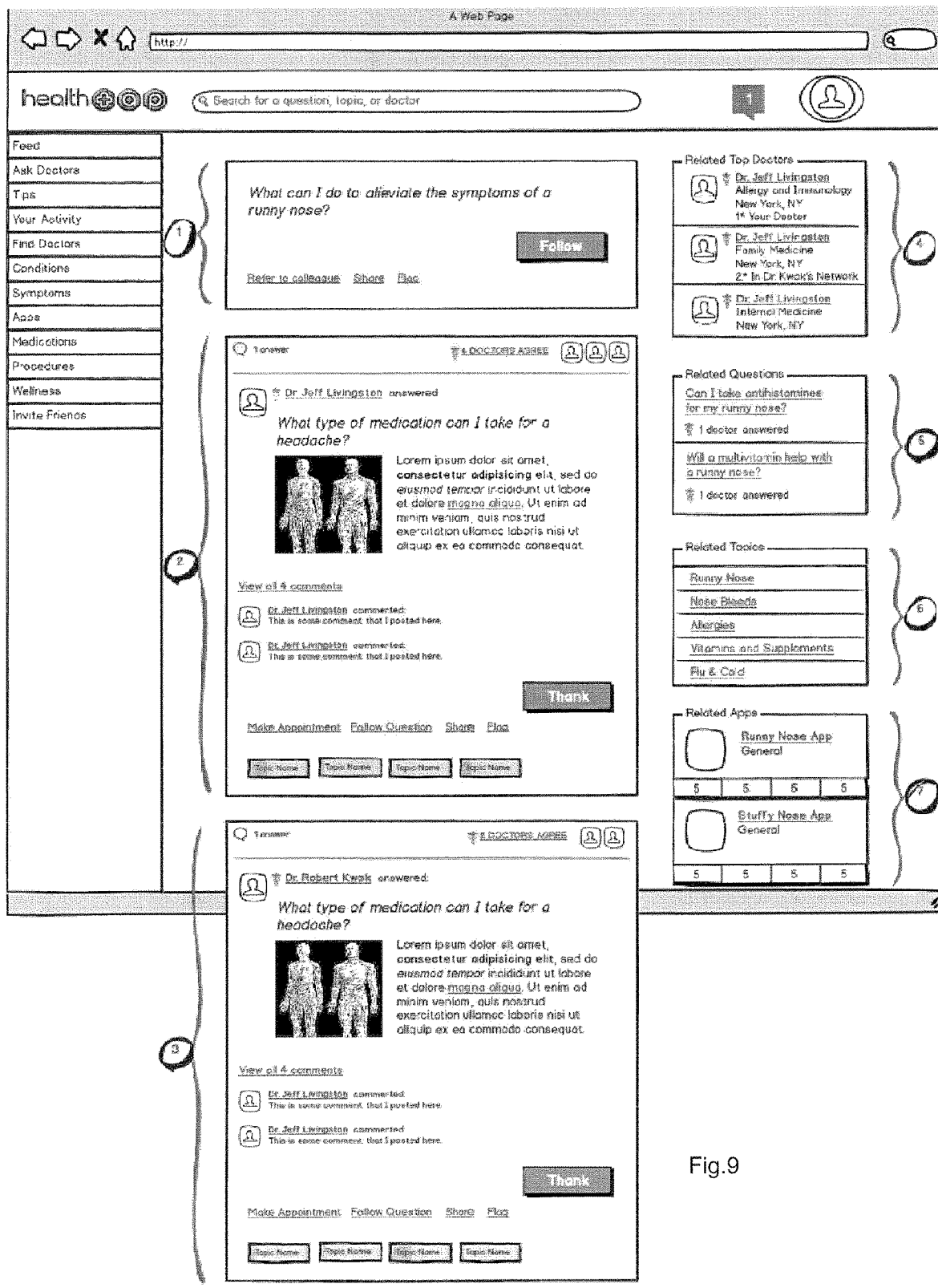
FIG. 9 illustrates a webpage or other graphical user interface (the "Answer Presentation Page") which is accessible by any user of the system, in accordance with embodiments of the present disclosure.

After a question is answered, the answer will be processed by the system and presented to the patient user on the Answer Presentation Page (e.g., when the user logs into the system 60 using a patient device 610) (shown in FIG. 9). The Answer Presentation Page is also accessible by other users by searching key words. In addition, the system 60 can also present related contents to the question on the Answer Presentation Page. For example, top doctors in related practicing area, related health tips, related medication information, and so on may be presented to the user on the Answer Presentation Page.

Figure 7:
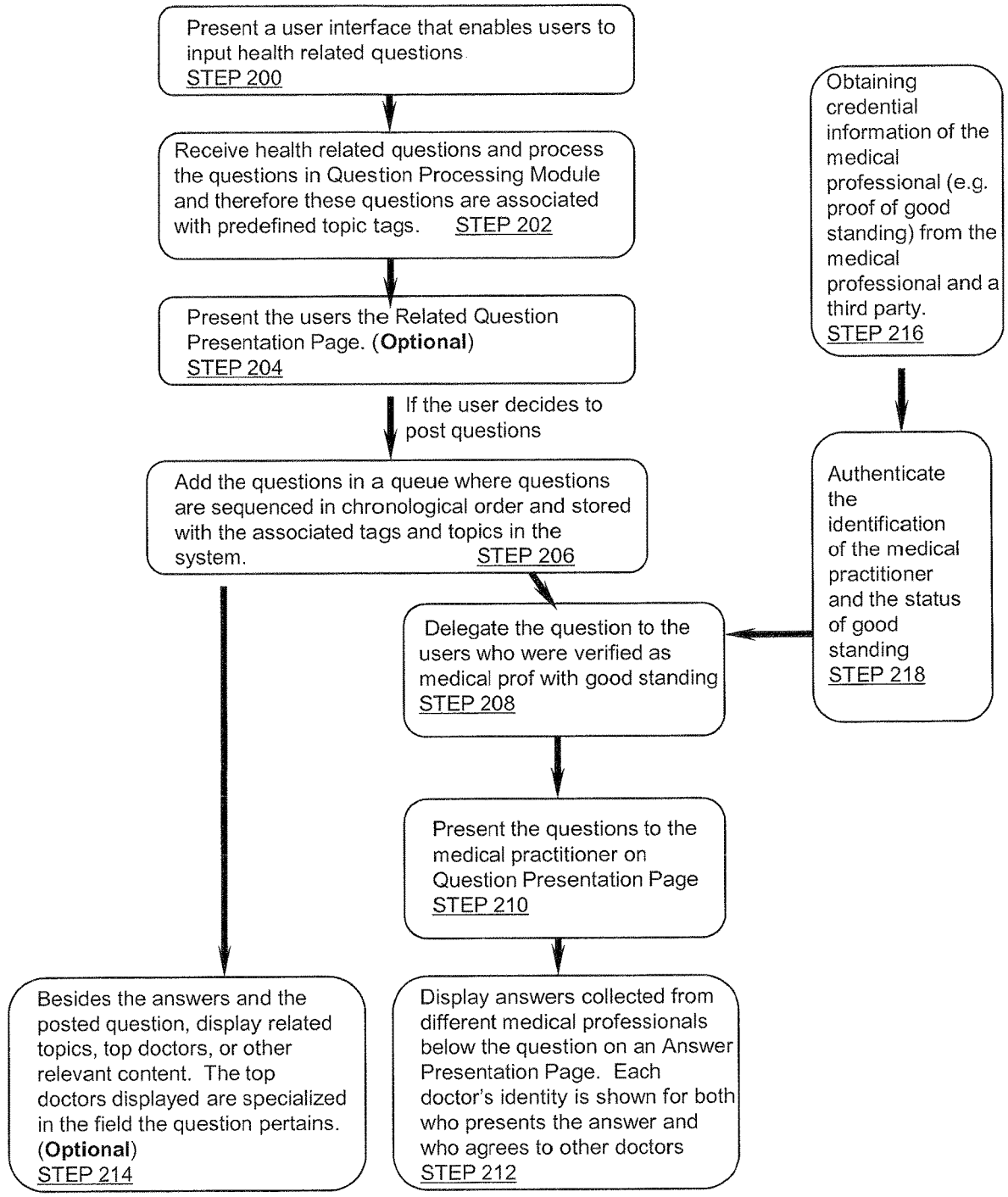
FIG. 7 is a flowchart illustrating a method for providing answers to user-submitted questions, in accordance with embodiments of the present disclosure.

FIG. 7 is a flowchart illustrating a method for providing answers to user-submitted questions, in accordance with the first exemplary embodiment of the present disclosure. As shown at Step 200, a user can post a question through the user interface provided on the patient device 610. At Step 202, the questions are received and processed by the Question Processing Module 606 after it is input by the user and the key words are extracted from the input content. The key words are then matched with topic tags which are previously generated and stored in the system 60. If one or multiple matches are established, such tags will be then assigned to the question and the association relationship will be stored in the data storage media. Such association can be based on content match between the keywords and the tags because the input question in the box is received as a string which is a system recognizable formality.

These topic tags can recognize misspellings, singular and plural forms and different expression of the same term. Thus the topic tags organize and correctly categorize the questions under the same topic tags even though the key words from the questions may be misspelled or expressed in a different term.

For example, a patient user inputs a question: "what can be the cause of chest pain and short of breath?" The system 60 then extracts the keywords "cause," "chest pain" and "short of breath" from the question and matches them with the existing tags. "Chest pain" and "short of breath" themselves can be existing topic tags. Or another topic tag such as "heart attack" can be assigned to this question because chest pain and shortness of breath are typical symptoms of heart attack. If the user misspelled "chest pain," the system can 60 still recognize it and associate the question with the right topic tag, "chest pain." In addition, the system 60 can also associate the medical term "myocardial infarction" with the topic tag "heart attack" where the former is a medical term of "heart attack" used by the doctors. Further, the system 60 might also associate the question with topic tags like "pericarditis," "hypertrophic cardiomyopathy," or "mitral valve prolapse," because chest pain is a common and possible symptom for these diseases as well.

After the first level of labeling, the question can be further assigned to a Group ID, for example, "cardiovascular disease." And this "cardiovascular disease" Group ID may include content, questions and answers related to the symptoms, treatments, procedures, medication, health tips, diet suggestions and the like for cardiovascular disease.

Therefore, in the above example, the topic tags "cause," "chest pain," "short of breath," "heart attack," "pericarditis," "hypertrophic cardiomyopathy," and "mitral valve prolapse" can be assigned to the provided question. At the same time, this question is also assigned a Group ID, "cardiovascular disease." The topic tags used in the examples herein are not exhaustive, and persons skilled in the relevant field will readily understand that other such topic tags may be applied to sort questions by topics and thus associate and organize related questions together.

The Group IDs are important for rendering similar or related content on the Answer Presentation Page. Since the content rendered related to the questions are all belonging to the same Group IDs.

After the system 60 processes the question, it will proceed to send the question to doctors and solicit answers. However, before sending the question to doctors, the system 60 takes some measures to efficiently process and generate answers to the questions. First, in order to speed answer delivery, unnecessary traffic should be avoided, e.g., avoid processing questions which have been answered before or in which similar issues have been addressed. Therefore, the system 60 provides users (mainly patient users) an opportunity for a second thought before posting the question. This step includes presenting the patient users with a list of questions which are identified by the system 60 (e.g., by the Question Processing Module 606) that are either similar or related to the question the user just posted (FIG. 7, Step 204). These existing related questions are stored in the system 60 (e.g., in Data Storage Media 620) together with their associated tags and topics. The Question Processing Module 606 organizes these existing questions based on the multiple tags associated with them assigned by the system 60.

The delivery of the similar questions (and their answers) requires the system 60 derive a list of existing questions that are most related to the question posted. Such relevancy is computed by the system 60 through analyzing and matching the tags between the existing questions and the present question. The list of related previous questions will be presented in a descending order of relevancy. For example, the similar questions and answers that have exactly the same tags with the posted question will be presented first. Then the similarity of the tags will be analyzed and the existing questions sharing most closely related tags will be presented second. If a question cannot be matched with similar questions based on the relevancy of the tags, the content within the same Group ID as the input question will be presented to the user.

After being presented with previous questions, the user has an option to make the final decision to decide whether his or her question has been answered or not. In this embodiment, after reviewing the presented existing answers, some users might decide that their questions already have been addressed and they will not proceed to post the question. In this way, at least certain amount of unnecessary traffic will be reduced and the system 60 saves time and space to provide answers to questions that have not yet been answered. However, if the user decides his question has not been answered, the system will allow the user to proceed to post his/her own question.

After the question is posted by the user and processed and tagged by the system 60, it will be placed in a queue in reverse chronological order by Queue Management Module 602 (Step 206). Then the Queue Management Module 602 will selectively send questions to doctors based on information about the doctors stored in or accessible to the system 60 (e.g., doctor profile data). Such selective presentation of the questions to the doctors allows for more efficient and higher quality answers to the questions, as the questions provided are tailored to the doctor's interests and specialties (e.g., sending doctor the questions asked by the patients from the same city or community) and the doctors can answer the question more efficiently and willingly. The questions are only presented to, and accessible by, doctors who are licensed and in good standing (Step 208). Credential information can be obtained at step 216 and the doctor's good standing can be authenticated, at step 218. At Step 210, the questions will be presented to the doctors on a Question Presentation Page (shown in FIG. 8).

FIG. 8 is an illustration of a webpage or other graphical user interface (the "Question Presentation Page"), which may be presented to doctors using the system 60. The Question Presentation Page includes a text input box 801 which may be utilized by a doctor user to input text, not only to provide answers, but also to post a question on their own behalf, or alternatively, enter keywords to search for questions, topics, users, or other content. Under the text input box 801, there is a frame (section 3) soliciting health tips (meaning short, doctor-written notes in areas like beauty, diet, exercise or parenting, which may be provided to users when logged into the system 60, or may be delivered by text message or e-mail) from the doctors. Questions to be answered are listed below the text box (Section 4). Options to provide additional answers to the questions already answered and to indicate agreement with already-provided answers may also provided on the Question Presentation Page (Section 5).

Section 4 of the Question Presentation Page exemplifies how questions are presented to the doctors. Even though there is only one question shown in Section 4 of the Question Presentation Page, there may be more than one such unanswered questions presented to the doctors in Section 4. Such a list of unanswered questions can be questions only related to the doctor's specialty (claimed by himself/herself or assigned by the system), or related to different specialties. The system 10 can have a default setting to send the questions to a doctor only within the doctor's specialty.

The questions presented to the doctors are sorted and provided by Queue Management Module 602 and are ordered based on the following considerations:

a. Time of submission: if a question was sitting in the system 60 for a long time, it is more likely to be sent to the doctor and more likely shows up on the top of the list of the questions on the Question Presentation Page.

b. The patient user's special request for a fast answer: the system 60 can set an option for the user to request for a fast answer. Upon such a request, this question will be tagged and automatically be processed first and placed on the top of the question queue presented on the Question Presentation Page.

c. Relation to the specialty the doctor claimed: As stated before, the doctor can identify his specialty or the system 60 can assign him a specialty. If the doctor does not specify whether he wants to receive the question within his own specialty only, the system 60 will send questions to the doctor within in his specialty by default. However, the doctor can choose to answer questions outside of his specialty. In a situation where a question has been sitting for a long time in the system 60, the doctor may be offered an award for providing an answer.

d. The geographic location of the doctor: As shown in FIG. 8, the doctor can see the geographic location of the user who solicits the answer. In addition, the system 60 (i.e., the Queue Management Module 602) will preferably send the questions to doctors who have closer geographic location to the patient user who posted the question. This function will endorse the communications between the patient and the doctor users in the same geographical area, which will create opportunities for the patient to find a doctor he/she likes within the same or close community. Similarly, doctors can develop future business through such communication.

e. whether the doctor has previously provided similar content or answers to similar questions: Since all the question and answers are tagged in the system 60, the answers and health tips the doctor provided can be recorded in the system 60. If a doctor provides some health related content or answers under certain topic tags, the system 60 will treat the doctor as being knowledgeable in this special topic or subject (e.g., by associating the doctor with particular topic tags). Thus, the system 60 may send the doctor questions closely related to what he has shown knowledge on.

After processing the questions, the Queue Management Module 602 will select certain question and send them to specific doctors based on the above consideration. These questions also are presented in a specific sequence or arrangement as a result of weighing some or all of the above considerations. This can be achieved by assigning a value, or a function to calculate such a value, to each consideration. As such, each question may obtain a sum value of the points computed under each consideration and the sum value determines the sequence of the questions presented to the doctor.

In addition, the system 60 may show the time the question was provided (top left corner in Section 4) so the doctor knows how old the question is. Also as shown in FIG. 9, there are also options for the doctor to refer the question to another doctor if he/she believes the other doctor is a specialist and is a better candidate to answer the question. This function helps direct the question to the doctor with right specialty and reduces the responding time.

Section 5 of FIG. 8 also shows questions that are already answered by other doctors. The doctor can either provide another answer in Section 5 or he can agree with the existing answers. This will help evaluate credibility of an answer provided by a doctor.

After a question is answered by one or many doctors, the answers will be sent back to the server 600 and stored, e.g., in data storage media 620. The system 60 will process these answers and assign topic tags and a Group ID to each answer, as described herein. After being processed and categorized, the answers will be presented to users on a Answer Presentation Page (Step 212).

FIG. 9 illustrates a webpage or other graphical user interface (the "Answer Presentation Page") which is accessible by any user of the system 60. As shown in FIG. 9, there are two answers provided by qualified doctors (Sections 2 and 3). This is only an exemplified way to show how the answers are presented. Each question may have many answers provided by the doctors. The sequence of how the answers are presented may be based on an Answer Score.

The Answer Score is a numeric or other value the system 60 assigns to each answer to reflect a level of confidence in the content of the answer. The Answer score is obtained based on: a. the reputation of the author of the answer; b. "agrees" the answer obtained from other doctor users; c. "thanks" the answer received from the patient users; d. times that the answer has been shared by users; e. the length of the answer (the longer answer has more details and will be given higher score). Such an Answer Score can be result value of a function of the above variables. Above variables can be given different weight toward computing such an Answer Score.

In addition, the answers provided by the doctor users are separately associated with topic tags based on the content of the answer and such topic tags are presented together with the answer (FIG. 9, Section 2 and Section 3, bottom line of boxes). This is similar to the process of tagging the questions. The system 60 will extract key words from the answers and process and match them with topic tags. After associating topic tags with the answer and recording such association in the system 60 (e.g., by storing the answer and associations with topic tags in data storage media 620), the system 60 is able to extract the answer when such answer are requested related to the topic tag. For example, in the step of presenting similar questions to the user before the user proceeds to post the question, not only the question is searched, but answers matching the topic tags are also searched and presented to the users. A related question with an associated answer having a high Answer Score will be more likely to be presented (or to be ranked higher or otherwise given priority in the sequence of presented answers) to the user on the Answer Presentation Page.

Further, the answers are presented along with the identity of the doctors who provided the answer. As shown in Section 2 and Section 3 of the Answer Presentation Page, the doctor's name and picture are presented along with the doctor's answer to the proposed question. In addition, a direct link to access the doctor's profile on the system 60 is provided to allow the patient learn the doctor's credentials.

Further, if the patient user is satisfied with the doctor's answer and wants to follow up, ask more questions or make an appointment for a doctor visit, the system 60 provides the patient access to do so.

There is also a showing of the "agrees" (i.e., an indication of agreement which may be provided, for example, by clicking a button labeled "agree") the doctor's answer received from other doctors. On top right corner of Section 2 in FIG. 9, it shows how many doctors have agreed with the answer and these "agreeing" doctors' identities are also provided to the user. By clicking any of the "agreeing" doctor's profile picture listed in the top right corner in Section 2 and Section 3 of FIG. 9, the user can learn more about each of "agreeing" doctors' identity and credibility in medical practice.

As shown in FIG. 9, Section 2 and Section 3, a "Thank" graphical user interface element is provided and the patient user can click it to express appreciation to the doctor who delivers the answer. The number of "Thanks" the doctor receives is counted by the system 60. On one hand, such "thanks" count can be a factor used by the system 60 to evaluate the doctor's performance. If a doctor receives more thanks, the system 60 generates a more favorable evaluation of the doctor. On the other hand, such "thanks" can also contribute to evaluate the quality of the answer. As stated above, the more thanks the answer receives, the higher Answer Score the answer will receive which will move the answer up in the showing queue (i.e., the answer will be ranked higher, thus causing the answer to be provided higher priority in the sequence of answers displayed to users).

In Section 1 of FIG. 9, next to the question, the user is also given an option to "follow" the question. By following a question, a user may be automatically notified by the system 60 of the updates related to this specific question. For example, if new answers are provided under this question, the user will be automatically notified of these new answers. Such notifications can be provided to users through the system 60, for example, by displaying the notification on a patient user device 610 when logged into the system 60, or may be provided by email, text or any other such electronic notification technologies.

Other than the answers to the question on the Answer Presentation Page, there are also other related content rendered to help the user acquire a comprehensive understanding of the pertinent issue (FIG. 7, step 214). For example, the top doctors in related practicing area (Section 4), related questions (Section 5), and related topics (Section 6) may be presented on the Answer Presentation Page. The Content Recommendation Module 604 will accomplish this task.

The list of top doctors presented on the Answer Presentation Page is provided based on matching the doctors' specialty with the topic tags. Further, doctors can be evaluated by their professional performance and the recognition the doctor received from other users. Any doctor evaluation or ranking system may be accessed by the Content Recommendation Module for obtaining relevant evaluation information. The top doctors (e.g., as determined based on evaluation or ranking information) having a matching specialty will be presented on the Answer Presentation Page.

The related questions and related topics are provided by the Content Recommendation Module 604 which matches the topic tags associated with the content (i.e., the content of information stored in data storage media 620, such as questions/answers, GroupIDs, topics, etc.) with topic tags associated with the questions. The more similar topic tags shared by the content and the questions, the more possibility the content will be presented on the Answer Presentation Page. In the situation that a question does not have content sharing matching tags, content under the same identifiable Group ID can be presented.

Virtual Consultations

In further embodiments, the present disclosure provides systems and methods for virtual consultations between a patient and a healthcare professional.

Figure 10:
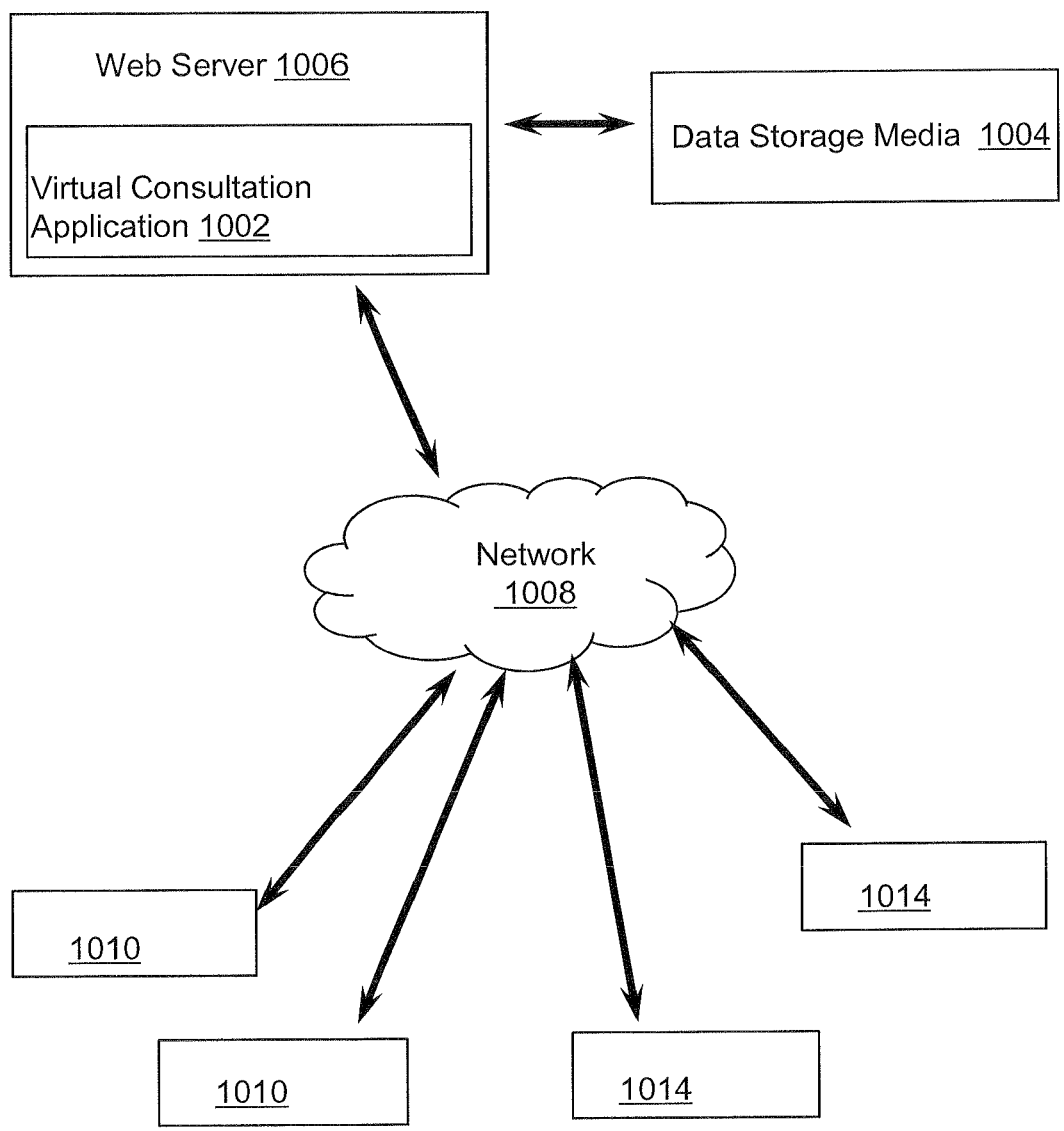
FIG. 10 is a schematic illustration of a system for virtual healthcare consultations, in accordance with embodiments of the present disclosure.

FIG. 10 is a schematic illustration of a system for virtual healthcare consultation 1000 (which may be referred to hereinafter as 'system 1000'), in accordance with embodiments provided by the present disclosure. As shown in FIG. 10, the system 1000 includes a virtual consultation application 1002 hosted at least partially on a web server 1006, and data storage media 1004. These components are described below and may be located on the same device (e.g., a server, mainframe, desktop Personal Computer (PC), laptop, mobile device (smart phone or tablet), Personal Digital Assistant (PDA), telephone, mobile phone kiosk, cable box, and another device) or may be located on separate devices connected by a net work (e.g., the internet, or the cloud infrastructure), with wired and/or wireless segments.

The virtual consultation application 1002 may be fully or partially hosted on the server 1006, and electronically accessible over at least one network system 1008. The network system 1008 may include any type of network infrastructure, such as the Internet, or any other wired, wireless and/or partially wired network. The server 1006, application 1002 and network system 1008 may include a variety of hardware and software components to provide successful functioning of the server 1006 and the application 1002, as is well-known within the art. Further, any features, characteristics, designs and/or functions that are known within the art may be included with the system 1000 to further enhance its efficiency. The application 1002 may include any computer-readable memory or databases, which may be stored in any computer-readable medium, and may be accessible by a computer processor. The application 1002 may further include or access computer program instructions which may cause a processor to perform any algorithms and/or functions described in this disclosure. The virtual consultation application 1002 may include or have access to one or more virtual consultation databases which may be stored, for example, in data storage media 1004.

The system may further include one or more patient computer devices 1010 and one or more healthcare professional computer devices 1020. The patient computer devices 1010 and healthcare professional computer devices 1020 may be any computerized devices capable of communicating with the application 1002, for example via a network system 1008. The one or more patient computer device 1010 may be operated by a patient user of the system 1000, and the one or more healthcare professional computer devices 1020 may be operated by any healthcare professional (or other professional), such as a primary care physician, medical doctor, nurse, medical staff or other medical professional, or any representative thereof.

The data storage media 1004 is a computer-readable storage medium, which may be any device or medium that can store code and/or data for use by a computer system. This includes, but not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed. The data storage media 1004 may store virtual consultation related information, including, for example, profile information for healthcare professionals available for virtual consultation, as well as profile and/or health-related information for patient users of the system.

The virtual consultation application 1002 provides an interface for live video, voice and/or chat, as well as email-based inbox consultations between patients (using patient computer device 1010) and a healthcare professionals (using healthcare professional computer device 1020).

Patients may initiate a virtual consultation with a healthcare professional user of the system 1000 by logging into or otherwise accessing the virtual consultation application 1002 using a patient computer device 1010. The application 1002 may request the patient to input information in response to questions or other prompts in order to acquire background information and/or documentation for use by a healthcare professional during the virtual consultation. For example, the application 1002 may first request that the user provide input information describing the reason for the virtual consultation. The patient may then enter information (e.g., using a keyboard or other input device) to describe the problem or questions for which he is seeking consultation with a healthcare professional.

The application 1002 may further provide the patient with an interface through which to attach a file, for use by a healthcare professional during the virtual consultation. For patient computer devices 1010 having an integrated or associated camera, photos may be taken or selected from the device 1010 photo gallery and then attached for use during the virtual consultation. Other files which may be available on the patient computer device 1010 (e.g., health-related records or other documents) may be selected by the patient and uploaded for attachment and use during the virtual consultation.

After receiving the reason for the patient's visit and/or any user-selected attachments, the application 1002 may allow the patient user to select whether a live consultation or an "inbox" or email-based consultation is desired. Selecting a live consultation initiates a live virtual consultation via video, voice and/or chat with a healthcare professional using a healthcare professional computer device 1014. Healthcare professionals (e.g., physicians) may be online and actively available for virtual consultations through the application 1002, or may be scheduled to be available on an "on-call" basis.

When the patient user submits a request for a live virtual consultation, the application 1002 may attempt to connect the patient with a healthcare professional based on the patient's input reason for the consultation (e.g., by selecting a healthcare professional having particular expertise or training in the field of the patient's problems or questions), the order of the patient with respect to other patients requesting a virtual consultation, whether the patient is a priority user of the system (e.g., a subscribing or paying user—there may be different tiers of subscription, for example) and/or any combination of such considerations. Further, the patient may select a particular healthcare professional with which to conduct a virtual consultation, in which case the patient may be notified when the healthcare professional will be available for consultation, and the application 1002 may further provide a scheduling tool to schedule the virtual consultation at a later time should that healthcare professional not be available at the time of the patient's request.

While the patient waits for the application 1002 to match the patient with a healthcare professional (e.g., by contacting the healthcare professional through computer device 1014 using an electronic message, prompt or the like), the application 1002 may display to the user information related to the patient's input reason for the virtual consultation. For example, the application may access information stored in data storage media 1004 to find answers to related questions or problems.

Once a healthcare professional has been contacted and accepted the request for a virtual consultation, the application 1002 provides an interface for the live consultation to take place between the patient (using patient computer device 1010) and the healthcare professional (using healthcare professional computer device 1014). The interface may include a video feed of the patient and/or healthcare professional (e.g., from a camera accessible by the patient device 1010 and/or healthcare professional device 1014), audio feed (e.g., from a microphone accessible by the patient device 1010 and/or healthcare professional device 1014) and/or a chat interface for text-based chat communication between the patient and the healthcare professional. Further, the interface provided by the application 1002 allows the healthcare professional to receive the attachments provided by the patient via the patient computer device 1010.

During the virtual consultation, the application 1002 may provide the healthcare professional with various tools for documenting and performing the consultation. For example, the application 1002 may provide in the virtual consultation interface a tool for entering the healthcare professional's notes and/or observations to be appended to a medical chart for the patient. Further, the application 1002 may provide an electronic prescription tool for facilitating or enabling the communication of prescription information from the healthcare professional to the patient, pharmacy information for looking up and displaying nearby pharmacies, a referral tool for referring the patient to other healthcare professional users of the system 1000 as well as to healthcare professionals who are not users of the system 1000. Any such information provided and/or produced during the virtual consultation may be stored and associated with the patient and/or healthcare professional within the system 1000, e.g., in data storage media 1004.

Records of the virtual consultations provided through the system 1000 may be stored and may further be made available to other healthcare professionals (e.g., healthcare professional users of the system 1000) for peer review. Reviewing healthcare professionals may rate various aspects of the virtual consultation, such as the appropriateness of medical treatment, clarity and actionability of patient instructions and thoroughness and quality of documentation. Such reviews may be utilized to rate the healthcare professional users of the system 1000.

Healthcare professionals may be compensated through the application 1002 for providing virtual consultations. Compensation may be based on a per consultation basis, a time-available basis or the like. Similarly, patient users may pay for virtual consultations through the system 1000 on a per consultation basis, on a subscription basis (e.g., subscribing users may receive some preset number of virtual consultations per month or other time-period) or the like.

The systems and methods provided herein may be integrated or otherwise incorporated into a single platform for delivering healthcare services to users. For example, the healthcare professional evaluation systems (e.g., as shown and described with respect to FIGS. 1 and 3), the system for providing answers to user-submitted questions (e.g., as shown and described with respect to FIG. 6) and/or the system for facilitating virtual consultations may be integrated into a single platform accessible to patients and healthcare professionals (e.g., utilizing patient computer devices and healthcare professional computer devices), thus enabling a variety of functionalities and delivery of healthcare services through a single portal, accessible to users through the Internet.

While the invention has been described with respect to a limited number of embodiments, it is not intended to be exhaustive or to limit the invention to the precise forms disclosed. Persons skilled in the art, having benefit of this disclosure, can appreciate that many modifications and variations are possible in light of the above disclosure. For example, the systems and methods provided herein may be advantageously employed for use by other professionals or persons having particular expertise in any given field, including, lawyers, professors, accountants, contractors, bankers and so on. Accordingly, the scope of the invention should be limited only by the following claims.

Many other variations and modifications may be made to the above-described embodiments of the disclosure without departing substantially from the spirit and principles of the disclosure. All such modifications and variations are intended to be included herein within the scope of the present disclosure and protected by the following claims.

What is claimed is:

1. A computer-implemented method for improving communication efficiency and reducing data redundancy in a computerized platform, comprising:
    obtaining an inquiry from a user device connected to the computerized platform through a network connection;
    storing the inquiry in a queue of unanswered inquiries received from a plurality of user devices connected to the computerized platform;
    monitoring in real time, by a queue management module, respective durations of time for which individual inquiries, including the inquiry, remain unanswered in the queue;
    determining, by the queue management module, a priority value of the inquiry based, at least in part, on the monitoring, wherein the queue management module alters the priority value of the inquiry as the duration of time for which the inquiry remains unanswered in the queue increases;
    associating the inquiry with a set of topic labels;
    sorting, by a question processing module, at least a subset of previously-obtained inquiries based, at least in part, on (a) a quantity of common topic labels shared between the set of topic labels associated with the inquiry and a respective set of topic labels associated with each previously-obtained inquiry in the subset and (b) a quality score associated with an answer to each previously-obtained inquiry in the subset to generate a sorted list;
    causing presentation, via the user device, of the sorted list;
    responsive to the presentation of the sorted list, receiving user interactions via the user device;
    routing, by the queue management module, at least the inquiry from the queue to be presented via a computer device associated with a healthcare professional, based at least partially on (a) the user interactions, (b) the priority value of the inquiry, and (c) at least one of a user request, relation to a specialty of the healthcare professional, geographic location of the healthcare professional, or history of answers provided by the healthcare professional;
    determining, before obtaining an answer to the inquiry, a time limit for requesting modification of the inquiry based, at least in part, on a traffic volume of the computerized platform;
    determining that the time limit has elapsed;
    responsive to determining that the time limit has elapsed, transmitting to the user device a request to modify the inquiry;
    responsive to presentation of the inquiry via the computer device associated with the healthcare professional, obtaining the answer to the inquiry; and
    causing presentation, via the user device, of the answer to the inquiry.

2. The method of claim 1, wherein associating the inquiry with a set of topic labels comprises associating the inquiry with at least one of a topic tag or a Group ID based on content of the inquiry.

3. The method of claim 1, further comprising routing inquiries exclusively to the healthcare professional, wherein the healthcare professional has good standing with a professional medical oversight body.

4. The method of claim 1, further comprising providing profile information of healthcare professionals to users.

5. The method of claim 1, wherein the quality score associated with an answer is based on at least one of a reputation of an author of the answer, a number of concurrences of the answer, a number of positive feedbacks to the answer, or a length of the answer.

6. A system, comprising:
    a plurality of user devices, each having a non-transitory memory and a processor; and
    a server positioned remote from the plurality of user devices and having a non-transitory memory storing contents that, when executed by one or more computer processors coupled to the memory, cause the system to:
        obtain an inquiry from a user device of the plurality of user devices;
        store the inquiry in a queue of unanswered inquiries received from the plurality of user devices;
        monitor, in real time, respective durations of time for which individual inquiries, including the inquiry, remain unanswered in the queue;
        determine a priority value of the inquiry based, at least in part, on the monitoring, wherein the priority value of the inquiry is altered as the duration of time for which the inquiry remains unanswered in the queue increases;
        associate the inquiry with a set of topic labels;
        sort at least a subset of previously-obtained inquiries based, at least in part, on (a) a quantity of common topic labels shared between the set of topic labels associated with the inquiry and a respective set of topic labels associated with each previously-obtained inquiry in the subset and (b) a quality score associated with an answer to each previously-obtained inquiry in the subset to generate a sorted list;
        cause presentation, via the user device, of the sorted list;
        responsive to the presentation of the sorted list and user instructions received via the user device, route at least the inquiry from the queue to be presented via a computer device associated with a healthcare professional, based at least partially on (a) the priority value of the inquiry and (b) at least one of a user request, relation to a specialty of the healthcare professional, geographic location of the healthcare professional, or history of answers provided by the healthcare professional;

determine, before obtaining an answer to the inquiry, a time limit for requesting modification of the inquiry based, at least in part, on a traffic volume of the system;

determine that the time limit has elapsed;

responsive to the determination that the time limit has elapsed, transmit to the user device a request to modify the inquiry;

responsive to presentation of the inquiry via the computer device associated with the healthcare professional, obtaining the answer to the inquiry; and cause presentation, via the user device, of the answer to the inquiry.

7. The system of claim 6, wherein the set of topic labels associated with the inquiry includes at least one of a topic tag or a Group ID based on content of the inquiry.

8. The system of claim 6, wherein the contents further cause the system to route inquiries exclusively to the healthcare professional, wherein the healthcare professional has good standing with a professional medical oversight body.

9. The system of claim 6, wherein the contents further cause the system to provide profile information of healthcare professional users to users.

10. The system of claim 6, wherein the quality score associated with an answer is based on at least one of a reputation of an author of the answer, a number of concurrences of the answer, a number of positive feedbacks to the answer, or a length of the answer.

11. A computer-readable storage medium not constituting a transitory medium, the computer-readable storage medium storing contents that, when executed by one or more processors, cause the one or more processors to perform actions comprising:

obtaining an inquiry from a user device;

storing the inquiry in a queue of unanswered inquiries received from a plurality of user devices;

monitoring, in real time, respective durations of time for which individual inquiries, including the inquiry, remain unanswered in the queue;

determining a priority value of the inquiry based, at least in part, on the monitoring, wherein the priority value of the inquiry is altered as the duration of time for which the inquiry remains unanswered in the queue increases;

associating the inquiry with a set of topic labels;

sorting at least a subset of previously-obtained inquiries based, at least in part, on (a) a quantity of common topic labels shared between the set of topic labels associated with the inquiry and a respective set of topic labels associated with each previously-obtained inquiry in the subset and (b) a quality score associated with an answer to each previously-obtained inquiry in the subset to generate a sorted list;

causing presentation, via the user device, of the sorted list;

routing at least the inquiry from the queue to be presented via a computer device associated with a healthcare professional, based at least partially on (a) the priority value of the inquiry and (b) at least one of a user request, relation to a specialty of the healthcare professional, geographic location of the healthcare professional, or history of answers provided by the healthcare professional;

determining, before obtaining an answer to the inquiry, a time limit for requesting modification of the inquiry based, at least in part, on a received traffic volume;

determining that the time limit has elapsed;

responsive to determining that the time limit has elapsed, transmitting to the user device a request to modify the inquiry;

responsive to presentation of the inquiry via the computer device associated with the healthcare professional, obtaining the answer to the inquiry; and causing presentation, via the user device, of the answer to the inquiry.

12. The computer-readable storage medium of claim 11, wherein associating the inquiry with a set of topic labels comprises associating the inquiry with at least one of a topic tag or a Group ID based on content of the inquiry.

13. The computer-readable storage medium of claim 11, wherein the actions further comprise routing inquiries exclusively to the healthcare professional, wherein the healthcare professional has good standing with a professional medical oversight body.

14. The computer-readable storage medium of claim 11, wherein the actions further comprise providing profile information of healthcare professionals to users.

15. The computer-readable storage medium of claim 11, wherein the quality score associated with an answer is based on at least one of a reputation of an author of the answer, a number of concurrences of the answer, a number of positive feedbacks to the answer, or a length of the answer.

* * * * *